(12) United States Patent
Jeffrey et al.

(10) Patent No.: US 11,819,512 B2
(45) Date of Patent: Nov. 21, 2023

(54) SOLID FORMS OF A CD73 INHIBITOR AND THE USE THEREOF

(71) Applicant: ARCUS BIOSCIENCES, INC., Hayward, CA (US)

(72) Inventors: Jenna Leigh Jeffrey, Oakland, CA (US); Kenneth V. Lawson, San Francisco, CA (US); Dillon Harding Miles, Berkeley, CA (US)

(73) Assignee: ARCUS BIOSCIENCES, INC., Hayward, CA (US)

( * ) Notice: Subject to any disclaimer, the term of this patent is extended or adjusted under 35 U.S.C. 154(b) by 184 days.

(21) Appl. No.: 17/311,945

(22) PCT Filed: Dec. 12, 2019

(86) PCT No.: PCT/US2019/065916
§ 371 (c)(1),
(2) Date: Jun. 8, 2021

(87) PCT Pub. No.: WO2020/123772
PCT Pub. Date: Jun. 18, 2020

(65) Prior Publication Data
US 2022/0062313 A1    Mar. 3, 2022

Related U.S. Application Data

(60) Provisional application No. 62/779,064, filed on Dec. 13, 2018.

(51) Int. Cl.
*A01N 43/04* (2006.01)
*A61K 31/70* (2006.01)
*A61K 31/706* (2006.01)
*A61K 33/243* (2019.01)
*A61K 31/282* (2006.01)
*A61K 31/704* (2006.01)
*C07H 19/23* (2006.01)

(52) U.S. Cl.
CPC .......... *A61K 31/706* (2013.01); *A61K 31/282* (2013.01); *A61K 31/704* (2013.01); *A61K 33/243* (2019.01); *C07H 19/23* (2013.01)

(58) Field of Classification Search
None
See application file for complete search history.

(56) References Cited

U.S. PATENT DOCUMENTS

| | | |
|---|---|---|
| 9,090,697 B2 | 7/2015 | Sim |
| 10,239,912 B2 | 3/2019 | Debien et al. |
| 10,981,944 B2 | 4/2021 | Debien et al. |
| 11,001,603 B2 | 5/2021 | Debien et al. |
| 2017/0267710 A1 | 9/2017 | Debien et al. |
| 2020/0405629 A1 | 12/2020 | Jaen et al. |
| 2021/0371449 A1 | 12/2021 | Debien et al. |
| 2021/0395291 A1 | 12/2021 | Pennell et al. |

FOREIGN PATENT DOCUMENTS

| | | |
|---|---|---|
| WO | 2015/164573 A1 | 10/2015 |
| WO | 2017/120508 A1 | 7/2017 |
| WO | 2017/120508 A8 | 7/2017 |
| WO | 2019/173682 A1 | 9/2019 |
| WO | 2020/123772 A1 | 6/2020 |

OTHER PUBLICATIONS

U.S. Appl. No. 17/193,473, filed Mar. 5, 2021.
U.S. Appl. No. 17/206,896, filed Mar. 19, 2021.
International Search Report dated Feb. 28, 2020 corresponding to PCT/US2019/065916 filed Dec. 12, 2019; 3 pages.
Written Opinion of the International Search Authority dated Feb. 28, 2020 corresponding to PCT/US2019/065916 filed Dec. 12, 2019; 4 pages.
International Search Report and Written Opinion dated Oct. 7, 2021 corresponding to PCT/US2021/037535 filed Jun. 16, 2021; 16 pages.
Caira, Mino R. et al., "Crystalline Polymorphism of Organic Compounds," *Topics in Current Chemistry* (Jan. 1, 1998) 198:163-208.
Extended European Search Report for European Application No. 19896971.9 dated Jul. 4, 2022. 8 pages.

*Primary Examiner* — Patrick T Lewis
(74) *Attorney, Agent, or Firm* — SHEPPARD MULLIN RICHTER & HAMPTON LLP

(57) ABSTRACT

Solid forms of Compound I, which modulates the conversion of AMP to adenosine by 5'-nucleotidase, ecto, and compositions containing the compound and methods for preparing the solid forms, are described herein. The use of such solid form of Compound I and compositions for the treatment and/or prevention of a diverse array of diseases, disorders and conditions, including cancer- and immune-related disorders, that are mediated by 5'-nucleotidase, ecto is also provided.

17 Claims, 9 Drawing Sheets

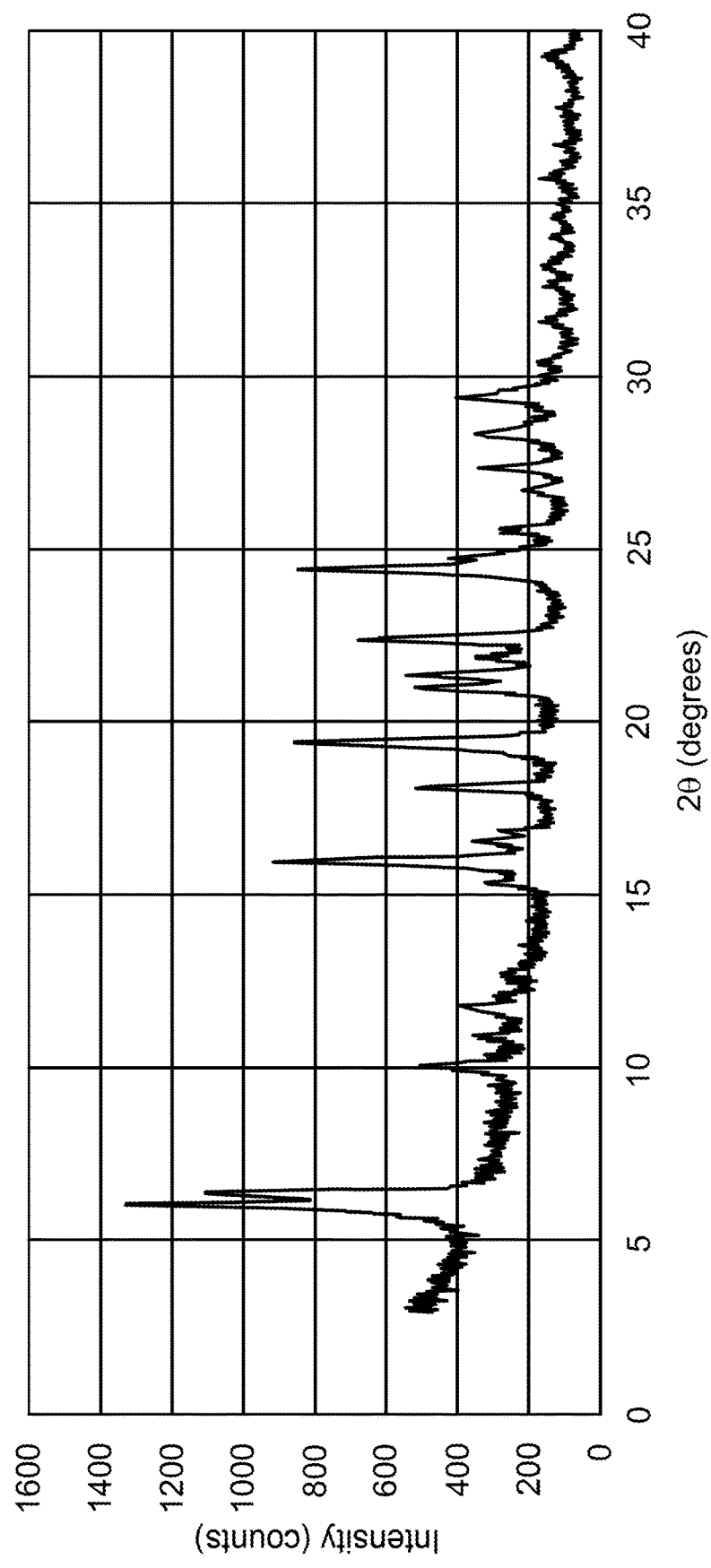
Figure 1: XRPD Pattern of Form A

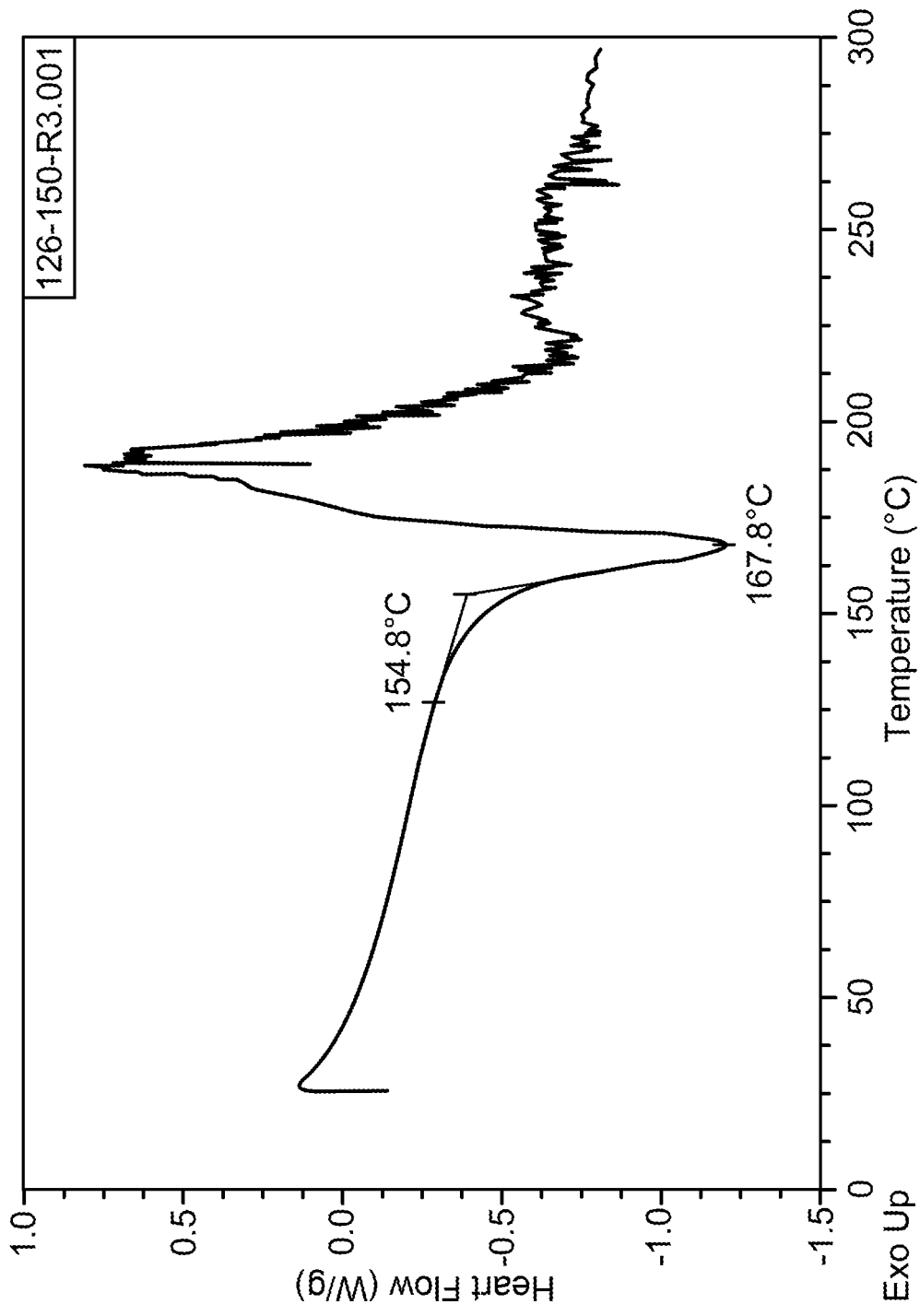
Figure 2: DSC Trace of Form A

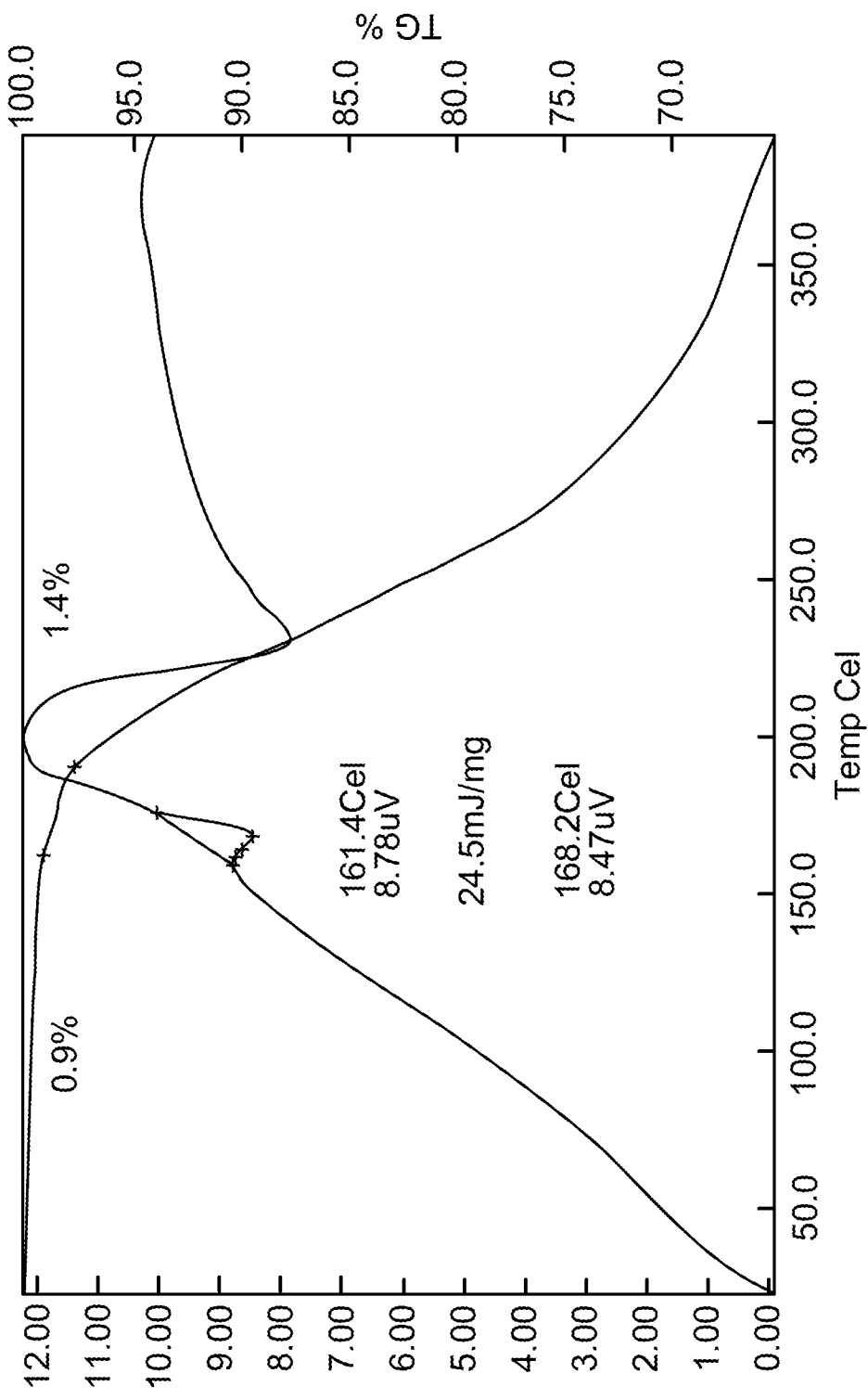
Figure 3: TGA/DTA Trace of Form A

FIG. 4

Figure 4: Single Crystal X-Ray Diffraction Unit Cell Data

| Empirical formula | C24 H30 Cl F N6 O9 P2 |
|---|---|
| Crystal system | Monoclinic |
| Space group | P 1 21 1 |
| A | 16.6099(8) Å |
| B | 4.8116(2) Å |
| C | 20.0513(11) Å |
| Α | 90° |
| Β | 90.386(2)° |
| Γ | 90° |
| Z | 2 |
| Volume | 1602.47(13) Å$^3$ |
| Density (calculated) | 1.374 g/cm$^3$ |

FIG. 5

Figure 5: Selected Crystallization Conditions

| Conditions | Crystal Form | Melting Point (°C) |
|---|---|---|
| Amorphous | N/A | 132-164 |
| Solution of compound in hot methanol, add acetonitrile, cool | Form B | 161-166 |
| Solution of compound in hot ethanol, add acetonitrile, cool | Form B | 161-166 |
| Solution of compound in hot ethanol, add acetonitrile, cool, place collected solvent under vacuum at 60 °C for 24 hours | Form A | 164-170 |
| Compound exposed to 75% relative humidity at 40 °C for 2 weeks | Form C (poorly crystalline) | N.D. |
| Saturated solution of compound in 7:3 acetone:water, allow solvent to evaporate | Form D (poorly crystalline) | N.D. |

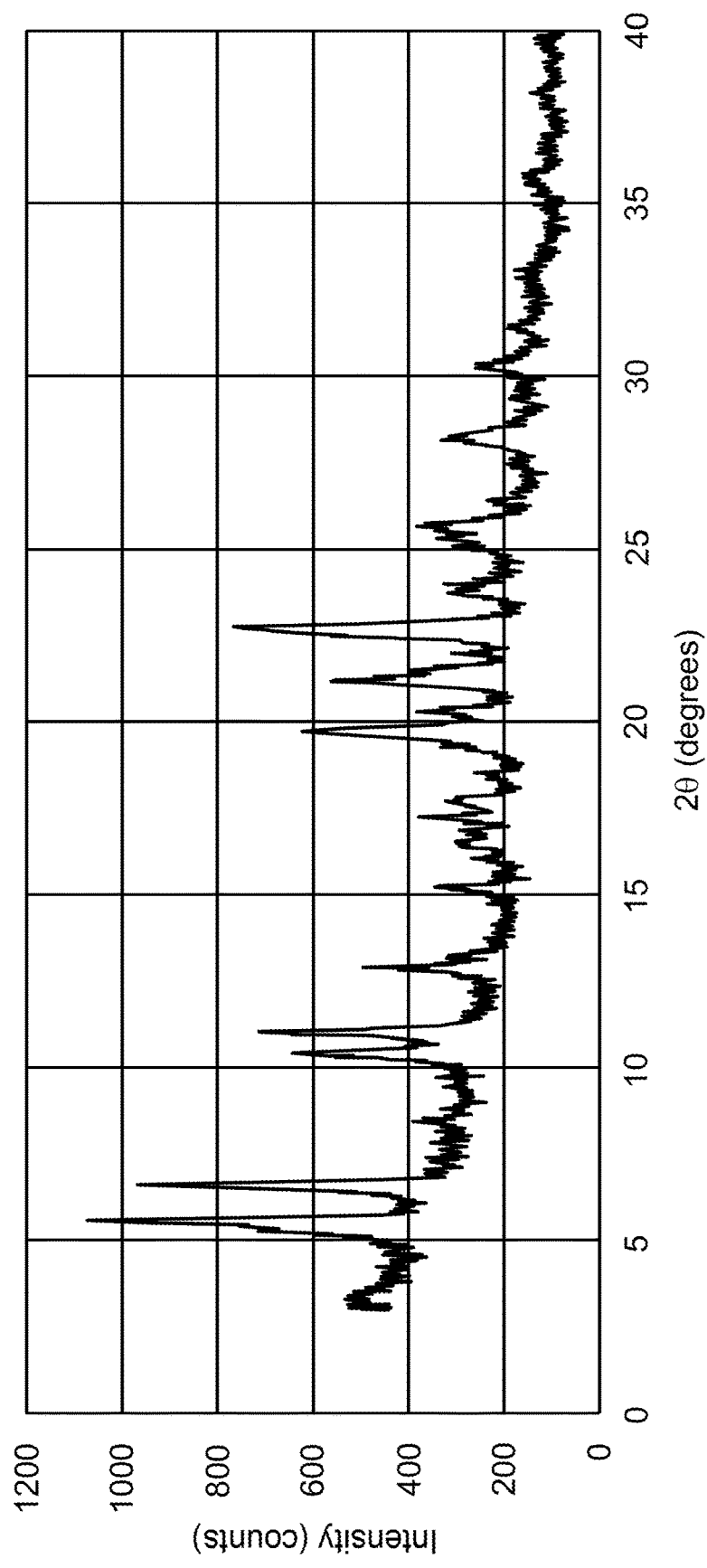
Figure 6: XRPD Pattern of Form B

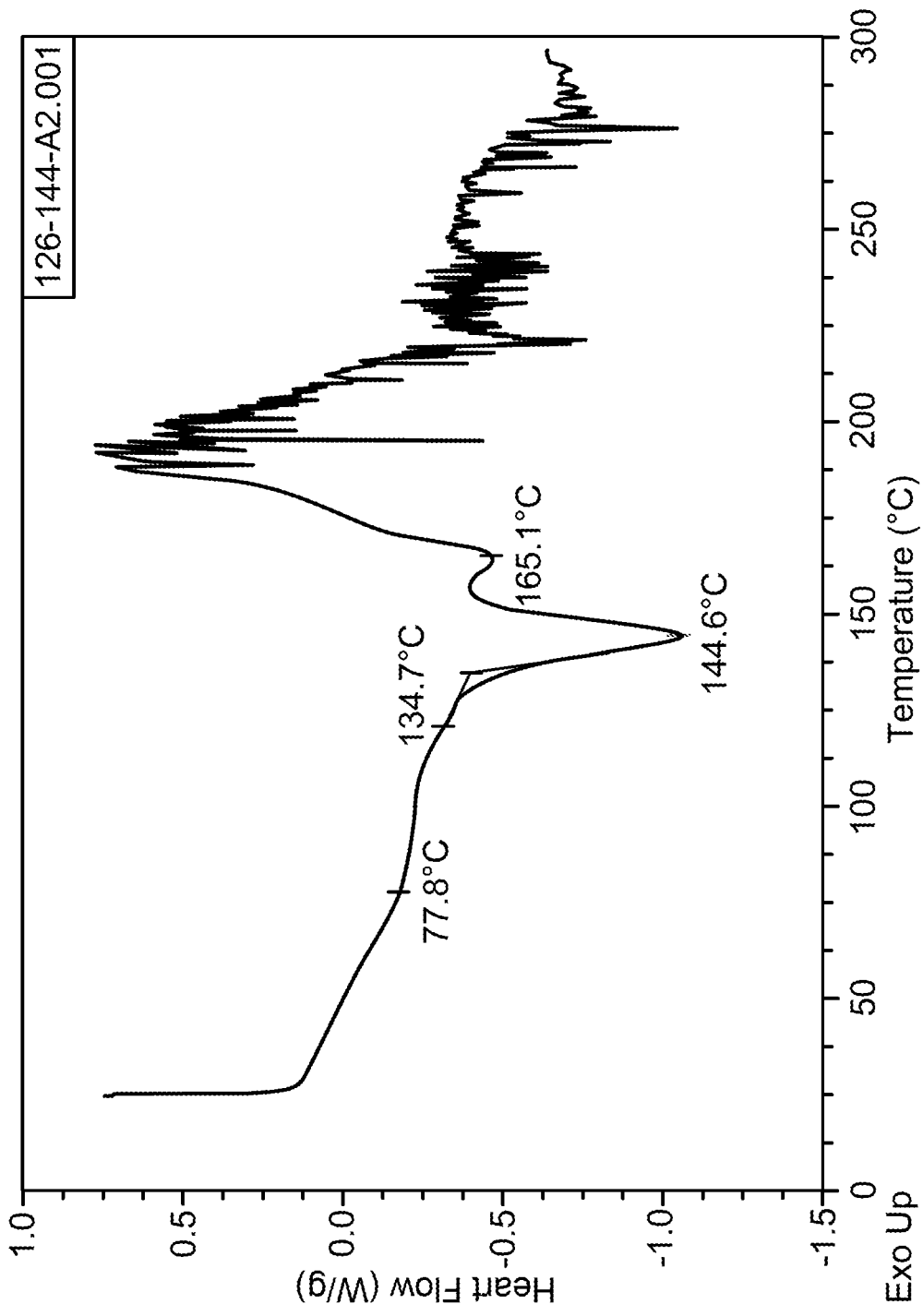

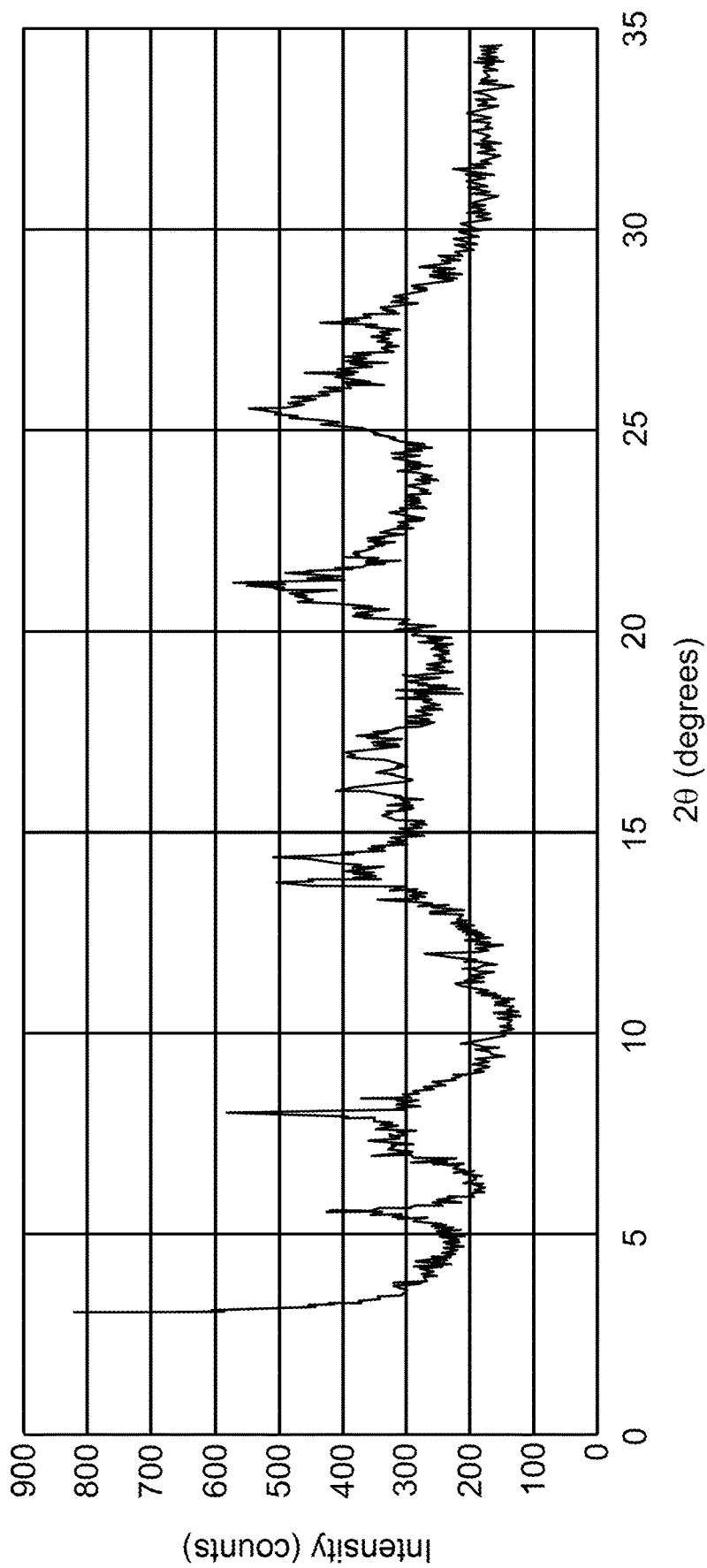
Figure 8: XRPD Pattern of Form C

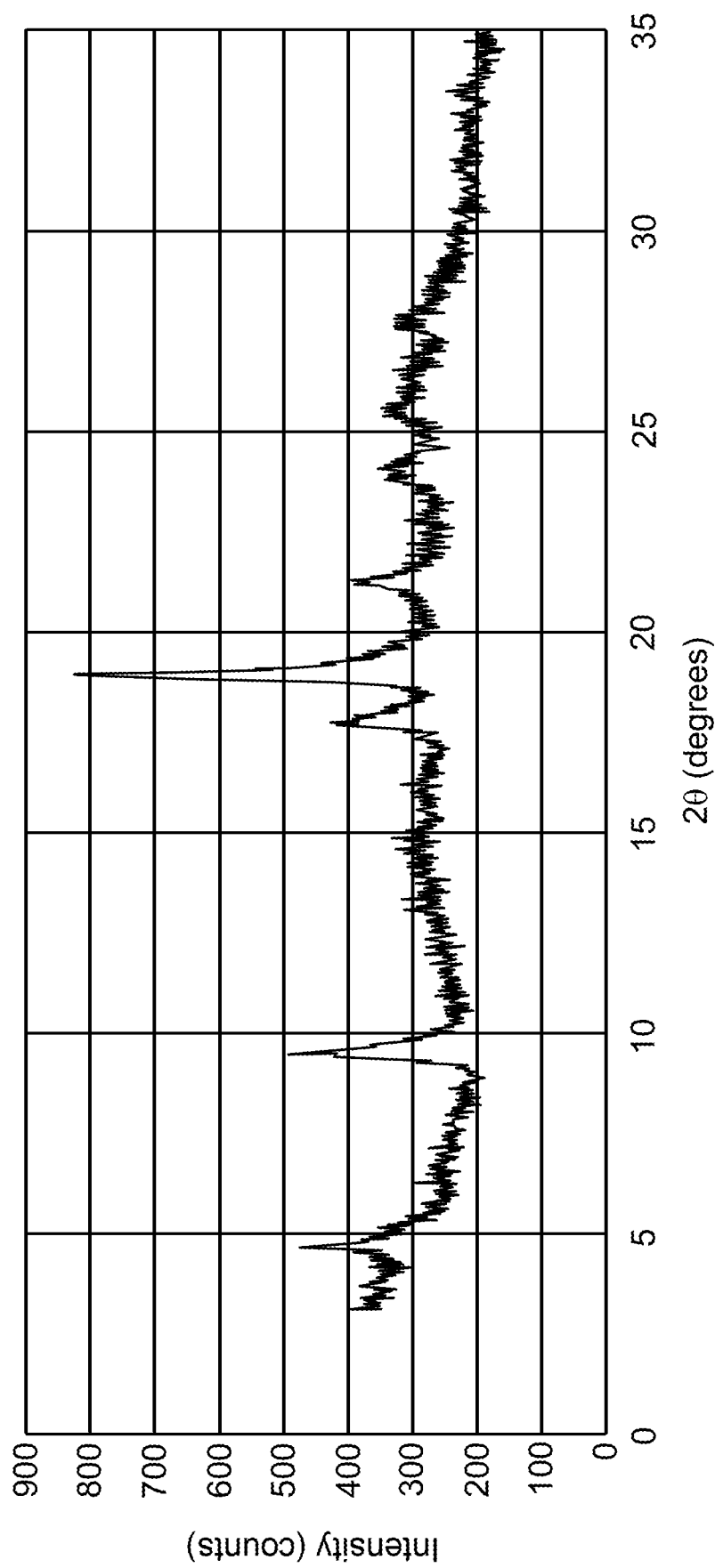
Figure 9: XRPD Pattern of Form D

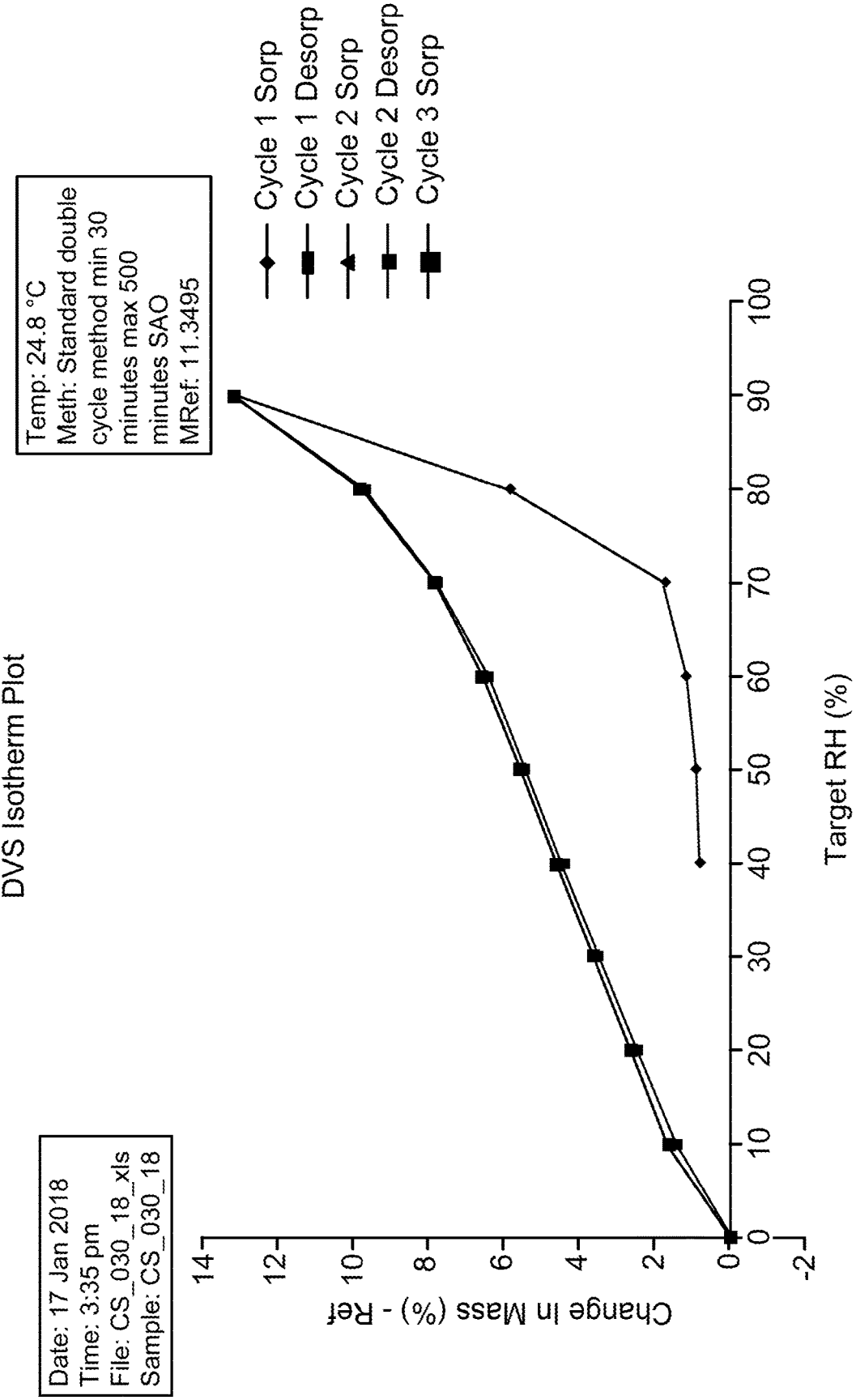
Figure 10: Dynamic Vapor Sorption Isotherm Plot of Form A

SOLID FORMS OF A CD73 INHIBITOR AND THE USE THEREOF

CROSS-REFERENCES TO RELATED APPLICATIONS

This application claims the benefit of priority to U.S. Provisional Application No. 62/779,064, filed on Dec. 13, 2018, the contents of which are herein incorporated by reference for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD

Provided herein are, for example, solid forms of a compound and compositions for inhibition of adenosine by 5'-nucleotidase, ecto, also known as CD73, and pharmaceutical compositions comprising same. Also provided herein are, for example, methods of treating or preventing a disease, disorder or condition, or a symptom thereof, mediated by inhibition of adenosine by 5'-nucleotidase, ecto.

BACKGROUND OF THE INVENTION

Ectonucleotides catalyze the conversion of ATP to adenosine, an endogenous modulator that impacts multiple systems, including the immune system, the cardiovascular system, the central nervous system, and the respiratory system. Adenosine also promotes fibrosis in a variety of tissues. In the first step of the production of adenosine, ectonucleoside triphosphate diphosphohydrolase 1 (ENTPD1), also known as CD39 (Cluster of Differentiation 39), hydrolyzes ATP to ADP, and then ADP to AMP. In the next step, AMP is converted to adenosine by 5'-nucleotidase, ecto (NT5E or 5NT), also known as CD73 (Cluster of Differentiation 73).

The enzymatic activities of CD39 and CD73 play strategic roles in calibrating the duration, magnitude, and chemical nature of purinergic signals delivered to various cells (e.g., immune cells). Alteration of these enzymatic activities can change the course or dictate the outcome of several pathophysiological events, including cancer, autoimmune diseases, infections, atherosclerosis, and ischemia-reperfusion injury, suggesting that these ecto-enzymes represent novel therapeutic targets for managing a variety of disorders.

CD73 inhibition with monoclonal antibodies, siRNA, or small molecules delays tumor growth and metastasis (Stagg, J. (2010) PNAS U.S.A. 107:1547-52). For example, anti-CD73 antibody therapy was shown to inhibit breast tumor growth and metastasis in animal models (Stagg, J. (26 Jan. 2010) PNAS U.S.A, 107(4):1547-52). In addition, the use of antibodies that specifically bind CD73 has been evaluated for the treatment of bleeding disorders (e.g., hemophilia) (U.S. Pat. No. 9,090,697). Recently, there have been several efforts to develop therapeutically useful CD73 small molecule inhibitors. For example, Bhattarai et al. ((2015) J Med Chem 58:6248-63) have studied derivatives and analogs of α,β-Methylene-ADP (AOPCP), one of the most metabolically stable, potent and selective CD73 inhibitors known, and purine CD73 derivatives have been reported in the patent literature (WO 2015/164573). However, the development of small molecules has been hampered due to, for example, less than ideal metabolic stability.

The compound (((((2R,3S,4R,5R)-5-(6-chloro-4-(((S)-1-(2-fluorophenyl)ethyl)amino)-1H-pyrazolo[3,4-b]pyridin-1-yl)-3,4-dihydroxytetrahydrofuran-2-yl)methoxy)(hydroxy)-phosphoryl)methyl)phosphonic acid, designated herein as Compound I, is a potent and selective small-molecule inhibitor of CD73. In view of the role played by CD73 in cancer, as well as a diverse array of other diseases, disorders and conditions, and the current lack of CD73 inhibitors available to medical practitioners, there is a need for stable solid forms of Compound I, as well as compositions and methods associated therewith.

BRIEF SUMMARY OF THE INVENTION

The present invention relates to solid forms of a compound that modulates the conversion of AMP to adenosine by 5'-nucleotidase, ecto (NT5E or 5NT; also known as CD73), and compositions (e.g., pharmaceutical compositions) comprising the compound. Such a compound (in a solid form), including methods of preparation, methods of use, and compositions are described in detail below.

In one particular aspect, the present invention provides a solid form of a compound having Formula (I):

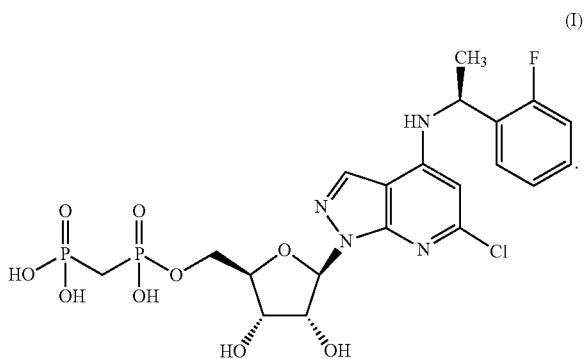 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F]

(I)

The present invention also relates to the use of the solid forms of such a compound and compositions for the treatment and/or prevention of a diverse array of diseases, disorders and conditions mediated, in whole or in part, by CD73. CD73 inhibitors have been linked to the treatment of a diverse array of disorders, including cancer, fibrosis, neurological and neurodegenerative disorders (e.g., depression and Parkinson's disease), cerebral and cardiac ischemic diseases, immune-related disorders, and disorders with an inflammatory component. [See, e.g., Sorrentino et al (2013) OncoImmunol, 2:e22448, doi: 10.4161/onci.22448; and Regateiro et al. (2012) Clin. Exp. Immunol, 171:1-7]. In particular embodiments, the solid forms of the compound described herein can be formulated in a manner to inhibit the immunosuppressive activity and/or the anti-inflammatory activity of CD73, and are useful as therapeutic or prophylactic therapy when such inhibition is desired. Unless otherwise indicated, when uses refer to the compound (or to the solid form of the compound) described herein, it is to be understood that such compound may be in the form of a composition (e.g., a pharmaceutical composition).

In some embodiments, the present invention contemplates methods for treating or preventing cancer in a subject (e.g., a human) comprising administering to the subject a therapeutically effective amount of a solid form of a compound of Formula (I). The present invention includes methods of treating or preventing a cancer in a subject by administering to the subject a solid form of a compound of Formula (I) in an amount effective to reverse, stop or slow the progression of CD73-mediated immunosuppression. In some embodiments, the CD73-mediated immunosuppression is mediated by an antigen-presenting cell (APC).

Examples of the cancers that can be treated using the solid form of a compound of Formula (I) and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, or Kaposi's sarcoma. Cancers that are candidates for treatment with a solid form of a compound of Formula (I) and compositions of the present invention are discussed further hereafter.

The present invention contemplates methods of treating a subject receiving a bone marrow transplant or peripheral blood stem cell transplant by administering a therapeutically effective amount of a solid form of a compound of Formula (I) sufficient to increase the delayed-type hypersensitivity reaction to tumor antigen, delay the time-to-relapse of post-transplant malignancy, increase relapse-free survival time post-transplant, and/or increase long-term post-transplant survival.

In certain embodiments, the present invention contemplates methods for treating or preventing an infective disorder (e.g., a viral infection) in a subject (e.g., a human) comprising administering to the subject a therapeutically effective amount of a solid form of a compound of Formula (I). In some embodiments, the infective disorder is a viral infection (e.g., a chronic viral infection), a bacterial infection, a fungal infection, or a parasitic infection. In certain embodiments, the viral infection is human immunodeficiency virus or cytomegalovirus.

In still other embodiments, the present invention contemplates methods for treating and/or preventing immune-related diseases, disorders and conditions; diseases having an inflammatory component; as well as disorders associated with the foregoing; with a solid form of a compound of Formula (I). Examples of immune-related diseases, disorders and conditions are described hereafter.

Other diseases, disorders and conditions that can be treated or prevented, in whole or in part, by modulation of CD73 activity are candidate indications for a solid form of a compound of Formula (I) as described herein.

The present invention further contemplates the use of the solid form of a compound of Formula (I) described herein in combination with one or more additional agents. The one or more additional agents may have some CD73-modulating activity and/or they may function through distinct mechanisms of action. In some embodiments, such agents comprise radiation (e.g., localized radiation therapy or total body radiation therapy) and/or other treatment modalities of a non-pharmacological nature. When combination therapy is utilized, the solid form of a compound of Formula (I) and the one additional agent(s) may be in the form of a single composition or multiple compositions, and the treatment modalities can be administered concurrently, sequentially, or through some other regimen. By way of example, the present invention contemplates a treatment regimen wherein a radiation phase is followed by a chemotherapeutic phase. The combination therapy can have an additive or synergistic effect. Other benefits of combination therapy are described hereafter.

BRIEF DESCRIPTION OF THE DRAWINGS

FIG. 1 shows an X-ray powder diffraction (XRPD) pattern of Compound I Form A.

FIG. 2 shows a differential scanning calorimetry (DSC) plot of Compound I Form A showing an endotherm at about 168° C., and an exotherm at about 188° C.

FIG. 3 shows a thermogravimetric analysis (TGA) of Compound I Form A.

FIG. 4 shows the single crystal X-Ray Diffraction Unit Cell Data for Compound I Form A.

FIG. 5 is a table showing a series of crystallization conditions for solid forms of Compound I.

FIG. 6 shows an X-ray powder diffraction (XRPD) pattern of Compound I Form B.

FIG. 7 shows a differential scanning calorimetry (DSC) plot of Compound I Form B.

FIG. 8 shows an X-ray powder diffraction (XRPD) pattern of Compound I Form C.

FIG. 9 shows an X-ray powder diffraction (XRPD) pattern of Compound I Form D.

FIG. 10 shows a dynamic vapor sorption isotherm plot of Form A.

DETAILED DESCRIPTION OF THE INVENTION

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

As used herein, the term "a solid form of a compound of Formula (I)" refers to any of the solid forms of the noted compound as described herein. The solid form can be, however, formulated to a liquid, gel, or ointment, for example, for ease of administration to a subject. In particular, with reference to a method involving the administration of a solid form of a compound of Formula (I), the method is meant to include administration of a liquid formulation that is prepared using the solid form of a compound of Formula (I).

The publications discussed herein are provided solely for their disclosure prior to the filing date of the present application. Further, the dates of publication provided may be different from the actual publication dates, which may need to be independently confirmed.

General

The compound (((((2R,3S,4R,5R)-5-(6-chloro-4-(((S)-1-(2-fluorophenyl)ethyl)amino)-1H-pyrazolo[3,4-b]pyridin-1-yl)-3,4-dihydroxytetrahydrofuran-2-yl)methoxy)(hydroxy)phosphoryl)methyl)phosphonic acid: (Compound I) is a potent inhibitor of CD73:

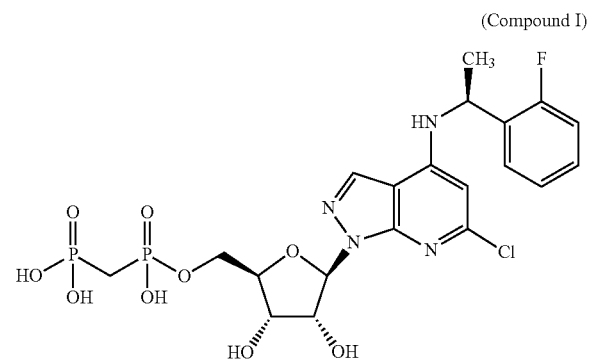 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F]

(Compound I)

The present invention results from the surprising discoveries of the solid forms of Compound I, advantages attributed to the forms as described herein, and processes for making the solid forms. Crystalline materials are generally more stable physically and chemically. The superior stability of crystalline material may make them more suitable to be used in the final dosage form as shelf life of the product is directly correlated with stability. A crystallization step in active pharmaceutical ingredient (API) processing also means an opportunity to upgrade the drug substance purity by rejecting the impurities to the processing solvent.

Definitions

Unless otherwise indicated, the following terms are intended to have the meaning set forth below. Other terms are defined elsewhere throughout the specification.

"Hydrate" refers to a complex formed by the combining of Compound I and water. The term includes stoichiometric as well as non-stoichiometric hydrates.

"Solvate" refers to a complex formed by the combining of Compound I and a solvent.

"Desolvated" refers to a Compound I form that is a solvate as described herein, and from which solvent molecules have been partially or completely removed. Desolvation techniques to produce desolvated forms include, without limitation, exposure of a Compound I Form (solvate) to a vacuum, subjecting the solvate to elevated temperature, exposing the solvate to a stream of gas, such as air or nitrogen, or any combination thereof. Thus, a desolvated Compound I form can be completely without solvent molecules, or partially solvated wherein solvent molecules are present in stoichiometric or non-stoichiometric amounts.

"Alcohol" refers to a solvent having a hydroxy group. Representative alcohols can have any suitable number of carbon atoms, such as $C_1$-$C_6$, and any suitable number of hydroxy groups, such as 1-3. Exemplary alcohols include, but are not limited to, methanol, ethanol, n-propanol, i-propanol, etc.

"Substantially free of other crystalline forms of Compound I" refers to a crystalline form of Compound I that contains less than 10% of other crystalline forms of Compound I. For example, substantially free can refer to a crystalline form of Compound I that contains less than 9, 8, 7, 6, 5, 4, 3, 2, or 1% of other crystalline forms of Compound I. Preferably, substantially free refers to a crystalline form of Compound I that contains less than 5% of other crystalline forms of Compound I. Preferably, substantially free refers to a crystalline form of Compound I that contains less than 1% of other crystalline forms of Compound I.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of CD73, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of CD73 or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an CD73 inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an CD73 inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of CD73, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Solid Forms of Compound I

The present invention provides solid forms of (((((2R,3S,4R,5R)-5-(6-chloro-4-(((S)-1-(2-fluorophenyl)ethyl)amino)-1H-pyrazolo[3,4-13]pyridin-1-yl)-3,4-dihydroxytetrahydrofuran-2-yl)methoxy)(hydroxy)phosphoryl)methyl) phosphonic acid: (Compound I), including crystalline and amorphous forms, as well as solvate and hydrate forms.

In some embodiments, the present invention provides a solid form, e.g., a crystalline form, of Compound I having the structure:

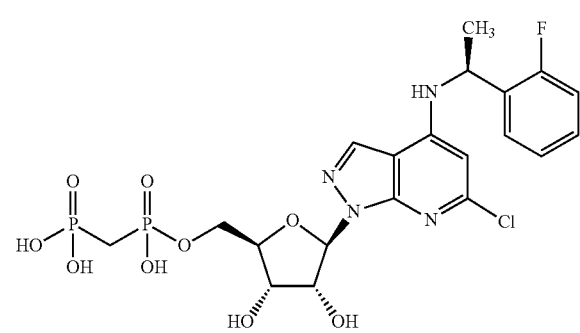 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F]

and solvates or hydrates thereof.

Compound I can adopt a variety of solid forms, including, but not limited to, Form A, Form B, Form C and Form D. Compound I can form a mixture of two or more crystalline forms, or form a single crystalline form substantially free of other crystalline forms.

Form A

In some embodiments, solid Form A of Compound I can be characterized by an X-ray powder diffraction pattern (XRPD) having peaks at 6.1, 6.4, 10.1, 11.7, 16, 16.6, 18.1, 19.4, 21, 21.4, 21.9, 22.4, 24.4, 25.6, 27.3, 28.3, and 29.4 degrees 2θ (±0.1 degrees 2θ), wherein the XRPD is made using CuK$_{α1}$ radiation, or a differential scanning calorimetry (DSC) plot characterized by a DSC endotherm at about 168° C. followed by a exotherm at about 188° C. The exotherm corresponds to sample decomposition. The solid Form A of Compound I can be characterized by both the aforementioned XRPD and DSC.

Form A of Compound I can be characterized by an X-ray powder diffraction (XRPD) pattern having one or more, e.g., two, three, four, five, or more, peaks at 6.1, 6.4, 10.1, 11.7, 16, 16.6, 18.1, 19.4, 21, 21.4, 21.9, 22.4, 24.4, 25.6, 27.3, 28.3, or 29.4 degrees 2θ (±0.1 degrees 2θ), wherein the XRPD is made using CuK$_{α1}$ radiation. In some embodiments, the solid Form A of Compound I can be characterized by an X-ray powder diffraction pattern having two or more peaks at 6.1, 6.4, 10.1, 11.7, 16, 16.6, 18.1, 19.4, 21, 21.4, 21.9, 22.4, 24.4, 25.6, 27.3, 28.3, or 29.4 degrees 2θ (±0.1 degrees 2θ), wherein the XRPD is made using CuK$_{α1}$ radiation. In some embodiments, the solid Form A of Compound I can be characterized by an X-ray powder diffraction pattern having three or more peaks at 6.1, 6.4, 10.1, 11.7, 16, 16.6, 18.1, 19.4, 21, 21.4, 21.9, 22.4, 24.4, 25.6, 27.3, 28.3, or 29.4 degrees 2θ (±0.1 degrees 2θ), wherein the XRPD is made using CuK$_{α1}$ radiation. In some embodiments, the solid Form A of Compound I can be characterized by an X-ray powder diffraction pattern having four or more peaks at 6.1, 6.4, 10.1, 11.7, 16, 16.6, 18.1, 19.4, 21, 21.4, 21.9, 22.4, 24.4, 25.6, 27.3, 28.3, or 29.4 degrees 2θ (±0.1 degrees 2θ), wherein the XRPD is made using CuK$_{α1}$ radiation. In some embodiments, the solid Form A of Compound I can be characterized by an X-ray powder diffraction pattern having five or more peaks at 6.1, 6.4, 10.1, 11.7, 16, 16.6, 18.1, 19.4, 21, 21.4, 21.9, 22.4, 24.4, 25.6, 27.3, 28.3, or 29.4 degrees 2θ (±0.1 degrees 2θ), wherein the XRPD is made using CuK$_{α1}$ radiation.

In some embodiments, the solid Form A of Compound I can be characterized by an X-ray powder diffraction pattern having six or more peaks at 6.1, 6.4, 10.1, 11.7, 16, 16.6, 18.1, 19.4, 21, 21.4, 21.9, 22.4, 24.4, 25.6, 27.3, 28.3, or 29.4 degrees 2θ (±0.1 degrees 2θ), wherein the XRPD is made using CuK$_{α1}$ radiation. In some embodiments, the solid Form A of Compound I can be characterized by an X-ray powder diffraction pattern having seven or more peaks at 6.1, 6.4, 10.1, 11.7, 16, 16.6, 18.1, 19.4, 21, 21.4, 21.9, 22.4, 24.4, 25.6, 27.3, 28.3, or 29.4 degrees 2θ (±0.1 degrees 2θ), wherein the XRPD is made using CuK$_{α1}$ radiation. In some embodiments, the solid Form A of Compound I can be characterized by an X-ray powder diffraction pattern having eight or more peaks at 6.1, 6.4, 10.1, 11.7, 16, 16.6, 18.1, 19.4, 21, 21.4, 21.9, 22.4, 24.4, 25.6, 27.3, 28.3, or 29.4 degrees 2θ (±0.1 degrees 2θ), wherein the XRPD is made using CuK$_{α1}$ radiation. In some embodiments, the solid Form A of Compound I can be characterized by an X-ray powder diffraction pattern having nine or more peaks at 6.1, 6.4, 10.1, 11.7, 16, 16.6, 18.1, 19.4, 21, 21.4, 21.9, 22.4, 24.4, 25.6, 27.3, 28.3, or 29.4 degrees 2θ (±0.1 degrees 2θ), wherein the XRPD is made using CuK$_{α1}$ radiation. In some embodiments, the solid Form A of Compound I can be characterized by an X-ray powder diffraction pattern having ten or more peaks at 6.1, 6.4, 10.1, 11.7, 16, 16.6, 18.1, 19.4, 21, 21.4, 21.9, 22.4, 24.4, 25.6, 27.3, 28.3, or 29.4 degrees 2θ (±0.1 degrees 2θ), wherein the XRPD is made using CuK$_{α1}$ radiation.

In some embodiments, the solid Form A of Compound I can be characterized by an XRPD pattern having peaks at 6.1, 6.4, and 16.0 degrees 2θ (±0.1 degrees 2θ), wherein the XRPD is made using CuK$_{α1}$ radiation. In some embodiments, the solid Form A of Compound I can be characterized by an X-ray powder diffraction (XRPD) pattern further comprising one or more peaks at 19.4, 21.4, 22.4, or 24.4 degrees 2θ (±0.1 degrees 2θ), wherein the XRPD is made using CuK$_{α1}$ radiation. In some embodiments, the solid Form A of Compound I can be characterized by an X-ray powder diffraction (XRPD) pattern further comprising two or more peaks at 19.4, 21.4, 22.4, or 24.4 degrees 2θ (±0.1 degrees 2θ), wherein the XRPD is made using CuK$_{α1}$ radiation. In some embodiments, the solid Form A of Compound I can be characterized by an X-ray powder diffraction (XRPD) pattern further comprising three or more peaks at 19.4, 21.4, 22.4, or 24.4 degrees 2θ (±0.1 degrees 2θ), wherein the XRPD is made using CuK$_{α1}$ radiation.

In some embodiments, the solid Form A of Compound I can be characterized by an X-ray powder diffraction (XRPD) pattern having peaks at 6.1, 6.4, 16.0, and 19.4 degrees 2θ (±0.1 degrees 2θ), wherein the XRPD is made using CuK$_{α1}$ radiation. In some embodiments, the solid Form A of Compound I can be characterized by an X-ray powder diffraction (XRPD) pattern having peaks at 6.1, 6.4, 16.0, 19.4, 21.4 and 24.4 degrees 2θ (±0.1 degrees 2θ), wherein the XRPD is made using CuK$_{α1}$ radiation. In some embodiments, the solid Form A of Compound I can be characterized by an X-ray powder diffraction (XRPD) pattern having peaks at 6.1, 6.4, 16.0, 19.4, 21.4, 22.4 and 24.4 degrees 2θ (±0.1 degrees 2θ), wherein the XRPD is made using CuK$_{α1}$ radiation. In some embodiments, the solid Form A of Compound I can be characterized by an X-ray powder diffraction (XRPD) pattern having peaks at 6.1, 6.4, 10.1, 16.0, 18.1, 19.4, 21.4, 22.4 and 24.4 degrees 2θ (±0.1 degrees 2θ), wherein the XRPD is made using CuK$_{α1}$ radiation. In some embodiments, the solid Form A of Compound I can be characterized by an X-ray powder diffraction (XRPD) pattern having peaks at 6.1, 6.4, 10.1, 16.0, 18.1, 19.4, 21.0, 21.4, 22.4 and 24.4 degrees 2θ (±0.1 degrees 2θ), wherein the XRPD is made using CuK$_{α1}$ radiation.

In some embodiments, the solid Form A of Compound I can be characterized by an XRPD pattern according to the peaks in Table 1 below, wherein the peaks are provided in degrees 2θ (±0.1 degrees 2θ), and wherein the XRPD is made using CuK$_{α1}$ radiation.

TABLE 1

XRPD Pattern Tabulated Peak Data of Form A

| 2θ | Intensity (counts) | Intensity (percent) |
| --- | --- | --- |
| 6.1 | 1338 | 120 |
| 6.4 | 1116 | 100 |
| 10.1 | 511 | 46 |
| 11.7 | 400 | 36 |
| 16.0 | 926 | 83 |
| 16.6 | 359 | 32 |
| 18.1 | 521 | 47 |
| 19.4 | 863 | 77 |
| 21.0 | 528 | 47 |
| 21.4 | 550 | 49 |
| 21.9 | 354 | 32 |
| 22.4 | 686 | 61 |
| 24.4 | 854 | 77 |
| 25.6 | 281 | 25 |
| 27.3 | 349 | 31 |
| 28.3 | 355 | 32 |
| 29.4 | 403 | 36 |

In some embodiments, the solid Form A of Compound I can be characterized by one or more characteristics of the single crystal x-ray diffraction data shown in FIG. 4.

Form B

In some embodiments, solid Form B of Compound I can be characterized by an X-ray powder diffraction pattern (XRPD) having peaks at 5.5, 6.6, 10.4, 11.0, 12.9, 15.2, 16.5, 17.2, 17.7, 19.7, 20.3, 21.2, 22.7, 24.0, 25.3, 25.6, 28.2 and 30.3 degrees 2θ (±0.1 degrees 2θ), wherein the XRPD is made using CuK$_{α1}$ radiation, or a differential scanning calorimetry (DSC) plot characterized by a DSC endotherm at about 145° C. followed by a exotherm at about 188° C. The exotherm corresponds to sample decomposition. The solid Form B of Compound I can be characterized by both the aforementioned XRPD and DSC.

Form B of Compound I can be characterized by an X-ray powder diffraction (XRPD) pattern having one or more, e.g., two, three, four, five, or more, peaks at 5.5, 6.6, 10.4, 11.0, 12.9, 15.2, 16.5, 17.2, 17.7, 19.7, 20.3, 21.2, 22.7, 24.0, 25.3, 25.6, 28.2 and 30.3 degrees 2θ (±0.1 degrees 2θ), wherein the XRPD is made using CuK$_{α1}$ radiation. In some embodiments, the solid Form B of Compound I can be characterized by an X-ray powder diffraction pattern having two or more peaks at 5.5, 6.6, 10.4, 11.0, 12.9, 15.2, 16.5, 17.2, 17.7, 19.7, 20.3, 21.2, 22.7, 24.0, 25.3, 25.6, 28.2 and 30.3 degrees 2θ (±0.1 degrees 2θ), wherein the XRPD is made using CuK$_{α1}$ radiation. In some embodiments, the solid Form B of Compound I can be characterized by an X-ray powder diffraction pattern having three or more peaks at 5.5, 6.6, 10.4, 11.0, 12.9, 15.2, 16.5, 17.2, 17.7, 19.7, 20.3, 21.2, 22.7, 24.0, 25.3, 25.6, 28.2 and 30.3 degrees 2θ (±0.1 degrees 2θ), wherein the XRPD is made using CuK$_{α1}$ radiation. In some embodiments, the solid Form B of Compound I can be characterized by an X-ray powder diffraction pattern having four or more peaks at 5.5, 6.6, 10.4, 11.0, 12.9, 15.2, 16.5, 17.2, 17.7, 19.7, 20.3, 21.2, 22.7, 24.0, 25.3, 25.6, 28.2 and 30.3 degrees 2θ (±0.1 degrees 2θ), wherein the XRPD is made using CuK$_{α1}$ radiation. In some embodiments, the solid Form B of Compound I can be characterized by an X-ray powder diffraction pattern having five or more peaks at 5.5, 6.6, 10.4, 11.0, 12.9, 15.2, 16.5, 17.2, 17.7, 19.7, 20.3, 21.2, 22.7, 24.0, 25.3, 25.6, 28.2 and 30.3 degrees 2θ (±0.1 degrees 2θ), wherein the XRPD is made using CuK$_{α1}$ radiation.

In some embodiments, the solid Form B of Compound I can be characterized by an X-ray powder diffraction pattern having six or more peaks at 5.5, 6.6, 10.4, 11.0, 12.9, 15.2, 16.5, 17.2, 17.7, 19.7, 20.3, 21.2, 22.7, 24.0, 25.3, 25.6, 28.2 and 30.3 degrees 2θ (±0.1 degrees 2θ), wherein the XRPD is made using CuK$_{α1}$ radiation. In some embodiments, the solid Form B of Compound I can be characterized by an X-ray powder diffraction pattern having seven or more peaks at 5.5, 6.6, 10.4, 11.0, 12.9, 15.2, 16.5, 17.2, 17.7, 19.7, 20.3, 21.2, 22.7, 24.0, 25.3, 25.6, 28.2 and 30.3 degrees 2θ (±0.1 degrees 2θ), wherein the XRPD is made using CuK$_{α1}$ radiation. In some embodiments, the solid Form B of Compound I can be characterized by an X-ray powder diffraction pattern having eight or more peaks at 5.5, 6.6, 10.4, 11.0, 12.9, 15.2, 16.5, 17.2, 17.7, 19.7, 20.3, 21.2, 22.7, 24.0, 25.3, 25.6, 28.2 and 30.3 degrees 2θ (±0.1 degrees 2θ), wherein the XRPD is made using CuK$_{α1}$ radiation. In some embodiments, the solid Form B of Compound I can be characterized by an X-ray powder diffraction pattern having nine or more peaks at 5.5, 6.6, 10.4, 11.0, 12.9, 15.2, 16.5, 17.2, 17.7, 19.7, 20.3, 21.2, 22.7, 24.0, 25.3, 25.6, 28.2 and 30.3 degrees 2θ (±0.1 degrees 2θ), wherein the XRPD is made using CuK$_{α1}$ radiation. In some embodiments, the solid Form B of Compound I can be characterized by an X-ray powder diffraction pattern having ten or more peaks at 5.5, 6.6, 10.4, 11.0, 12.9, 15.2, 16.5, 17.2, 17.7, 19.7, 20.3, 21.2, 22.7, 24.0, 25.3, 25.6, 28.2 and 30.3 degrees 2θ (±0.1 degrees 2θ), wherein the XRPD is made using CuK$_{α1}$ radiation.

In some embodiments, the solid Form B of Compound I can be characterized by an XRPD pattern having peaks at 5.5, 6.6 and 22.7 degrees 2θ (±0.1 degrees 2θ), wherein the XRPD is made using CuK$_{α1}$ radiation. In some embodiments, the solid Form B of Compound I can be characterized by an X-ray powder diffraction (XRPD) pattern further comprising one or more peaks at 10.4, 11, 19.7 or 21.2 degrees 2θ (±0.1 degrees 2θ), wherein the XRPD is made using CuK$_{α1}$ radiation. In some embodiments, the solid Form B of Compound I can be characterized by an X-ray powder diffraction (XRPD) pattern further comprising two or more peaks at 10.4, 11, 19.7 or 21.2 degrees 2θ (±0.1 degrees 2θ), wherein the XRPD is made using CuK$_{α1}$ radiation. In some embodiments, the solid Form B of Compound I can be characterized by an X-ray powder diffraction (XRPD) pattern further comprising three or more peaks at 10.4, 11, 19.7 or 21.2 degrees 2θ (±0.1 degrees 2θ), wherein the XRPD is made using CuK$_{α1}$ radiation.

In some embodiments, the solid Form B of Compound I can be characterized by an X-ray powder diffraction (XRPD) pattern having peaks at 5.5, 6.6, 11, and 22.7 degrees 2θ (±0.1 degrees 2θ), wherein the XRPD is made using CuK$_{α1}$ radiation. In some embodiments, the solid Form B of Compound I can be characterized by an X-ray powder diffraction (XRPD) pattern having peaks at 5.5, 6.6, 10.4, 11, 19.7 and 22.7 degrees 2θ (±0.1 degrees 2θ), wherein the XRPD is made using CuK$_{α1}$ radiation. In some embodiments, the solid Form B of Compound I can be characterized by an X-ray powder diffraction (XRPD) pattern having peaks at 5.5, 6.6, 10.4, 11.0, 12.9, 19.7, 21.2 and 22.7 degrees 2θ (±0.1 degrees 2θ), wherein the XRPD is made using CuK$_{α1}$ radiation.

In some embodiments, the solid Form B of Compound I can be characterized by an XRPD pattern according to the peaks in Table 3 below, wherein the peaks are provided in degrees 2θ (±0.1 degrees 2θ), and wherein the XRPD is made using CuK$_{α1}$ radiation.

TABLE 2

XRPD Pattern Tabulated Peak Data of Form B

| 2θ | Intensity (counts) | Intensity (percent) |
|---|---|---|
| 5.5 | 1082 | 100 |
| 6.6 | 976 | 90 |
| 10.4 | 646 | 60 |
| 11.0 | 717 | 66 |
| 12.9 | 495 | 46 |
| 15.2 | 342 | 32 |
| 16.5 | 305 | 28 |
| 17.2 | 363 | 34 |

TABLE 2-continued

XRPD Pattern Tabulated Peak Data of Form B

| 2θ | Intensity (counts) | Intensity (percent) |
|---|---|---|
| 17.7 | 326 | 30 |
| 19.7 | 628 | 58 |
| 20.3 | 385 | 36 |
| 21.2 | 562 | 52 |
| 22.7 | 766 | 71 |
| 24.0 | 322 | 30 |
| 25.3 | 343 | 32 |
| 25.6 | 385 | 36 |
| 28.2 | 334 | 31 |
| 30.3 | 264 | 24 |

In other embodiments, provided herein is a solid form of a compound of Formula (I), which is characterized as Form C or Form D.

In other embodiments, provided herein is a solid form of a compound of Formula (I), which is characterized as an amorphous form.

5'-Nucleotidase, Ecto and Inhibition Thereof

Human CD73 (also referred to as 5'-nucleotidase, ecto; NT5E; or 5NT) is a 574 amino acid residue protein (Accession No. AAH6593). Eukaryotic CD73 functions as a non-covalent homodimer with two structural domains, wherein the N- and C-terminal domains are connected by a hinge region that enables the enzyme to undergo large domain movements and switch between open and closed conformations (Knapp, K. et al. (2012) Structure 20:2161-73).

As used herein, the terms "CD73 inhibitor", "CD73 blocker", "adenosine by 5'-nucleotidase, ecto inhibitor", "NT5E inhibitor", "5NT inhibitor" and all other related art-accepted terms refer to a compound capable of modulating, either directly or indirectly, the CD73 receptor in an in vitro assay, an in vivo model, and/or other means indicative of therapeutic efficacy. The terms also refer to compounds that exhibit at least some therapeutic benefit in a human subject. An CD73 inhibitor may be a competitive, noncompetitive, or irreversible CD73 inhibitor. "A competitive CD73 inhibitor" is a compound that reversibly inhibits CD73 enzyme activity at the catalytic site; "a noncompetitive CD73 inhibitor" is a compound that reversibly inhibits CD73 enzyme activity at a non-catalytic site; and "an irreversible CD73 inhibitor" is a compound that irreversibly eliminates CD73 enzyme activity by forming a covalent bond (or other stable means of inhibiting enzyme function) with the enzyme.

CD73 inhibitors can modulate purinergic signaling, a type of extracellular signaling mediated by purine nucleotides and nucleosides such as ATP and adenosine. Purinergic signaling involves the activation of purinergic receptors in the cell and/or in nearby cells, resulting in the regulation of cellular functions. The enzymatic activity of CD73 plays a strategic role in calibrating the duration, magnitude, and chemical nature of purinergic signals delivered to various cells (e.g., immune cells). Alteration of these enzymatic activities can change the course or dictate the outcome of several pathophysiological events, including cancer, autoimmune and inflammatory diseases, infections, atherosclerosis, and ischemia-reperfusion injury, suggesting that these ecto-enzymes represent novel therapeutic targets for managing a variety of disorders.

Studies using tissues that overexpress CD73 and using CD73 knock-out mice have provided evidence that CD73 inhibitors have potential utility for melanomas, lung cancer, prostate cancer, and breast cancer (see, e.g., Sadej R. (2006)

Melanoma Res 16:213-22). Because higher expression levels of CD73 are associated with tumor neovascularization, invasiveness, resistance to chemotherapy, and metastasis, CD73 inhibitors can be used to control tumor progression and metastasis. Other potential utilities are discussed elsewhere herein.

Although the compound of Formula (I) is believed to exert its activity by inhibition of CD73, a precise understanding of the compound's underlying mechanism of action is not required to practice the invention. For example, the compound can also exert its activity, at least in part, through modulation (e.g., inhibition) of other components of the purinergic signaling pathway (e.g., CD39). The purinergic signaling system consists of transporters, enzymes and receptors responsible for the synthesis, release, action, and extracellular inactivation of (primarily) ATP and its extracellular breakdown product adenosine (Sperlagh, B. et al. (December 2012) Neuropsychopharmacologia Hungarica 14(4):231-38). There are several potential opportunities for modulation of the signaling process. However, as will be apparent to the skilled artisan, some of these opportunities are more tractable than others.

Methods of Synthesis

In general, the solid forms of Compound I are prepared using the methods described in the Examples below.

Modifications to Enhance Inhibitor Characteristics

It is frequently beneficial, and sometimes imperative, to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

Therapeutic and Prophylactic Uses

The present invention contemplates the use of a solid form of a compound of Formula (I) described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

Oncology-related Disorders. In accordance with the present invention, a solid form of a compound of Formula (I) can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer be metastatic or at risk of becoming metastatic, or may occur in a diffuse tissue, including cancers of the blood or bone marrow (e.g., leukemia). In some further embodiments, the solid form of a compound of Formula (I) can be used to overcome T-cell tolerance.

In some embodiments, the present invention provides methods for treating a proliferative condition, cancer, tumor, or precancerous condition with a solid form of a compound of Formula (I) and at least one additional therapeutic or diagnostic agent, examples of which are set forth elsewhere herein.

Immune-related Disorders and Disorders with an Inflammatory Component. As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the solid form of a compound of Formula (I) described herein such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The solid form of a compound of Formula (I) can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The solid form of a compound of Formula (I) can also be used to stimulate the immune system of patients suffering from iatrogenically-induced immune suppression, including those who have undergone bone marrow transplants, chemotherapy, or radiotherapy.

In particular embodiments of the present disclosure, the solid form of a compound of Formula (I) is used to increase or enhance an immune response to an antigen by providing adjuvant activity. In a particular embodiment, at least one antigen or vaccine is administered to a subject in combination with a solid form of a compound of Formula (I) to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with a solid form of a compound of Formula (I).

Microbial-related Disorders. By inhibiting the immunosuppressive and anti-inflammatory activity of CD73, the present invention contemplates the use of a solid form of a compound of Formula (I) described herein in the treatment and/or prevention of any viral, bacterial, fungal, parasitic or other infective disease, disorder or condition for which treatment with an CD73 inhibitor may be beneficial. Examples of such diseases and disorders include HIV and AIDS, staphylococcal and streptococcal infections (e.g., *Staphylococcus aureus* and *streptococcus sanguinis*, respectively), leishmania, toxoplasma, trichomonas, *Giardia, Candida albicans, Bacillus anthracis*, and *Pseudomonas aeruginosa*. Compounds of the invention can be used to treat sepsis, decrease or inhibit bacterial growth, and reduce or inhibit inflammatory cytokines.

CNS-related and Neurological Disorders. Inhibition of CD73 may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Other Disorders. Embodiments of the present invention contemplate the administration of a solid form of a compound of Formula (I) to a subject for the treatment or prevention of any other disorder that may benefit from at least some level of CD73 inhibition. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

In some embodiments, a solid form of a compound of Formula (I) may be used to inhibit statin-induced adenosine production, or reduce or decrease increases in blood glucose caused by a statin in a subject taking a statin (e.g., lovastatin and pravastatin)

Pharmaceutical Compositions

The solid form of a compound of Formula (I) may be in the form of compositions suitable for administration to a subject. In general, such compositions are "pharmaceutical compositions" comprising a solid form of a compound of Formula (I) and one or more pharmaceutically acceptable or physiologically acceptable diluents, carriers or excipients. In certain embodiments, the solid form of a compound of Formula (I) is present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., a solid form of a compound of Formula (I)) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of an CD73 inhibitor contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. A variety of drug delivery apparatus may be used to deliver a solid form of a compound of Formula (I), including implants (e.g., implantable pumps) and catheter systems, slow injection pumps and devices, all of which are well known to the skilled artisan.

Depot injections, which are generally administered subcutaneously or intramuscularly, may also be utilized to release the solid form of a compound of Formula (I) disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of a solid form of a compound of Formula (I) in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The solid forms of the compound of Formula (I) contemplated by the present invention may be in the form of any other suitable pharmaceutical composition (e.g., sprays for nasal or inhalation use) currently known or developed in the future.

Routes of Administration

The present invention contemplates the administration of a solid form of a compound of Formula (I), and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the solid form of a compound of Formula (I) disclosed herein over a defined period of time.

Particular embodiments of the present invention contemplate oral administration.

Combination Therapy

The present invention contemplates the use of a solid form of a compound of Formula (I) in combination with one or more active therapeutic agents. The additional active therapeutic agents can be small chemical molecules; macromolecules such as proteins, antibodies, peptibodies, peptides, DNA, RNA or fragments of such macromolecules; or cellular or gene therapies. In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, a solid form of a compound of Formula (I) is administered or applied sequentially, e.g., where one agent is administered prior to one or more other agents. In other embodiments, the agents are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The solid form of the compound of Formula (I) may be used in combination with at least one other (active) agent in any manner appropriate under the circumstances. In one embodiment, treatment with the at least one active agent and the solid form of the compound of Formula (I) is maintained over a period of time. In another embodiment, treatment with the at least one active agent is reduced or discontinued (e.g., when the subject is stable), while treatment with the solid form of the compound of Formula (I) is maintained at a constant dosing regimen. In a further embodiment, treatment with the at least one active agent is reduced or discontinued (e.g., when the subject is stable), while treatment with the solid form of the compound of Formula (I) is reduced (e.g., lower dose, less frequent dosing or shorter treatment regimen). In yet another embodiment, treatment with the at least one active agent is reduced or discontinued (e.g., when the subject is stable), and treatment with the solid form of the compound of Formula (I) is increased (e.g., higher dose, more frequent dosing or longer treatment regimen). In yet another embodiment, treatment with the at least one active agent is maintained and treatment with the solid form of the compound of Formula (I) is reduced or discontinued (e.g., lower dose, less frequent dosing or shorter treatment regimen). In yet another embodiment, treatment with the at least one active agent and treatment with the solid form of the compound of Formula (I) is reduced or discontinued (e.g., lower dose, less frequent dosing or shorter treatment regimen).

Oncology-related Disorders. The present invention provides methods for treating and/or preventing a proliferative condition, cancer, tumor, or precancerous disease, disorder or condition with a solid form of the compound of Formula (I) and at least one additional therapeutic or diagnostic agent.

In certain embodiments, the present invention provides methods for tumor suppression of tumor growth comprising administration of a solid form of the compound of Formula (I) described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in in immunomodulation can also be used in combination with the solid form of the compound of Formula (I) described herein for the suppression of tumor growth in cancer patients.

In other embodiments, the present invention provides methods for treating cancer in a subject, comprising administering to the subject a therapeutically effective amount of a solid form of a compound of Formula (I) and at least one chemotherapeutic agent. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

In some embodiments drawn to methods of treating cancer, the administration of a therapeutically effective amount of a solid form of a compound of Formula (I) in combination with at least one chemotherapeutic agent results in a cancer survival rate greater than the cancer survival rate observed by administering either agent alone. In further embodiments drawn to methods of treating cancer, the administration of a therapeutically effective amount of a solid form of a compound of Formula (I) in combination with at least one chemotherapeutic agent results in a reduction of tumor size or a slowing of tumor growth greater than reduction of the tumor size or tumor growth observed by administration of either agent alone.

Additional treatment modalities that may be used in combination with a solid form of the compound of Formula (I) include radiotherapy, a monoclonal antibody against a tumor antigen, a complex of a monoclonal antibody and toxin, a T-cell adjuvant, bone marrow transplant, or antigen presenting cells (e.g., dendritic cell therapy).

Immune Checkpoint Inhibitors. The present invention contemplates the use of the solid form of the compound of Formula (I) described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIGIT (T cell immunoreceptor with Ig and ITIM domains); TIM3 (T-cell membrane protein 3); LAG3 (lymphocyte activation gene 3); A2aR (adenosine A2a receptor A2aR); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

The present invention contemplates the use of the solid form of the compound of Formula (I) described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. The next class of immune checkpoint inhibitors to receive regulatory approval were against PD-1 and its ligands PD-L1 and PD-L2. Approved anti-PD1 antibodies include nivolumab (OPDIVO; Bristol-Myers Squibb) and pembrolizumab (KEYTRUDA; Merck) for various cancers, including squamous cell carcinoma, classical Hodgkin lymphoma and urothelial carcinoma. Approved anti-PDL1 antibodies include avelumab (BAVENCIO, EMD Serono & Pfizer), atezolizumab (TECENTRIQ; Roche/Genentech), and durvalumab (IMFINZI; AstraZeneca) for certain cancers, including urothelial carcinoma. While there are no approved therapeutics targeting TIGIT or its ligands CD155 and CD112, those in development include BMS-986207 (Bristol-Myers Squibb), MTIG7192A/RG6058 (Roche/Genentech), and OMP-31M32 (OncoMed).

Immune Modulators. The present invention contemplates the use of the solid form of the compound of Formula (I) described herein in combination with therapeutic agents that modulate the tumor microenvironment or augment or mediate immune responses. Examples of these agents include indoleamine 2,3-dioxygenase 1 (IDO-1) inhibitors, adenosine receptor antagonists and arginase inhibitors. IDO-1 breaks down tryptophan which impairs the activation of anti-tumor T cells. Similarly, arginase has been shown to be responsible for tumor immune escape through ARG-1, which depletes arginine from the tumor microenvironment leading to impaired T cell function such as stopped proliferation and secretion of cytokines. Adenosine signaling through $A_{2A}R$ and $A_{2B}R$ leads to the impairment of maturation and/or activation of T cells, NK cells and dendritic cells, which then impairs the activation of the immune system against cancer cells.

Metabolic and Cardiovascular Diseases. The present invention provides methods for treating and/or preventing certain cardiovascular- and/or metabolic-related diseases, disorders and conditions, as well as disorders associated therewith, with a solid form of the compound of Formula (I) and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the CD73 inhibitors described herein include various supplements and herbs (e.g., garlic, policosanol, and guggul).

The present invention encompasses pharmaceutically acceptable salts, acids or derivatives of any of the above.

Immune-related Disorders and Disorders Having an Inflammatory Component. The present invention provides methods for treating and/or preventing immune-related diseases, disorders and conditions; and diseases, disorders and conditions having an inflammatory component; with a solid form of the compound of Formula (I) and at least one additional therapeutic or diagnostic agent.

Examples of therapeutic agents useful in combination therapy are specific to the underlying disease, disorder or condition, and are known to the skilled artisan.

Microbial Diseases. The present invention provides methods for treating and/or preventing viral, bacterial, fungal and parasitic diseases, disorders and conditions, as well as disorders associated therewith, with a solid form of the compound of Formula (I) and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddl, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with a solid form of the compound of Formula (I) include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention contemplates the use of the solid form of the compound of Formula (I) described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present invention contemplate the use of the solid form of the compound of Formula (I) described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of antibacterial agents that are appropriate for use in specific bacterial infections.

Embodiments of the present invention contemplate the use of the solid form of the compound of Formula (I) described herein in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolies (e.g., 5-fluorocytosine).

Other Therapeutic Modalities. In another embodiment, the present invention contemplates the use of a solid form of the compound of Formula (I) in combination with adoptive cell therapy, a new and promising form of personalized immunotherapy in which immune cells with anti-tumor activity are administered to cancer patients. Adoptive cell therapy is being explored using tumor-infiltrating lymphocytes (TIL) and T cells engineered to express, for example, chimeric antigen receptors (CAR) or T cell receptors (TCR). Adoptive cell therapy generally involves collecting T cells from an individual, genetically modifying them to target a specific antigen or to enhance their anti-tumor effects, amplifying them to a sufficient number, and infusion of the genetically modified T cells into a cancer patient. T cells can be collected from the patient to whom the expanded cells are later reinfused (e.g., autologous) or can be collected from donor patients (e.g., allogeneic).

The present invention encompasses pharmaceutically acceptable salts, acids or derivatives of the agents (and members of the classes of agents) set forth above.

Dosing

The solid form of the compound of Formula (I) may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the solid form of the compound of Formula (I) may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the solid form of the compound of Formula (I) may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the solid form of the compound of Formula (I) is contained in a "unit dosage form". The phrase "unit dosage form" refers to physically discrete units, each unit containing a predetermined amount of the solid form of the compound of Formula (I), either alone or in combination with one or more additional agents, sufficient to produce the desired effect. It will be appreciated that the parameters of a unit dosage form will depend on the particular agent and the effect to be achieved.

Kits

The present invention also contemplates kits comprising a solid form of the compound of Formula (I), and pharmaceutical compositions thereof. The kits are generally in the form of a physical structure housing various components, as described below, and may be utilized, for example, in practicing the methods described above.

A kit can include a solid form of the compound of Formula (I) disclosed herein (provided in, e.g., a sterile container), which may be in the form of a pharmaceutical composition suitable for administration to a subject. The solid form of the compound of Formula (I) can be provided in a form that is ready for use (e.g., a tablet or capsule) or in a form requiring, for example, reconstitution or dilution (e.g., a powder) prior to administration. When the solid form of the compound of Formula (I) is in a form that needs to be reconstituted or diluted by a user, the kit may also include diluents (e.g., sterile water), buffers, pharmaceutically acceptable excipients, and the like, packaged with or separately from the solid form of the compound of Formula (I). When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbeco's Modification of Eagle's Medium; EDTA=ethylenediaminetetraacetic acid.

LC: Agilent 1100 series; Mass spectrometer: Agilent G6120BA, single quad
LC-MS method: Agilent Zorbax Eclipse Plus C18, 4.6×100 mm, 3.5 μM, 35° C., 1.5 mL/min flow rate, a 2.5 min gradient of 0% to 100% B with 0.5 min wash at 100% B; A=0.1% of formic acid/5% acetonitrile/94.9% water; B=0.1% of formic acid/5% water/94.9% acetonitrile
Flash column: ISCO Rf+
Reverse phase HPLC: ISCO-EZ; Column: Kinetex 5 μm EVO C18 100 A; 250×21.2 mm (Phenomenex)
Crystallization Methods In general, the morphology of the starting material is unimportant with respect to the successful recovery of crystalline material, although the kinetics of initial dissolution may be affected and a greater proportion of solvent may be required. For example, either amorphous material obtained via lyophilization or preexisting crystalline material may be used to obtain the desired crystalline form. In special cases, a metastable form is heated under vacuum to synthesize the desired form.

The sodium content of the starting material can also affect the success of the crystallization. In general, samples with a sodium content of 0.5% by weight or greater are more difficult to crystallize, although more solvent can be used to help mitigate this problem.

Single Solvents and Binary Solvent Mixtures

Several solvents can be used to generate the desired crystalline form, either through use of a single solvent or a binary solvent mixture. In the case of a single solvent the starting material is dissolved by heating in a solvent capable of forming a reasonably concentrated solution, followed by cooling to precipitate the desired crystalline form. Suitable solvents for use alone or as a mixture include but are not limited to isopropanol, ethanol, methanol, acetonitrile, acetic acid, and water.

Slow evaporation of a saturated solution of material in an appropriate solvent or mixture is also effective in obtaining crystalline material. In general, the sample has lower crystallinity as measured by XRPD. Suitable solvents include but are not limited to acetone, tetrahydrofuran, ethanol, methanol, acetonitrile, and water.

In the case of a binary solvent mixture, the material is first dissolved in a solvent capable of forming a reasonably concentrated solution as outlined above, and, either while the solution is still hot or has reached room temperature, addition of a less polar solvent in which the material is not readily soluble to precipitate the desired material. In a selected example, the material is dissolved in ethanol at room temperature and acetonitrile added to precipitate the desired crystalline form. Suitable precipitating solvents include but are not limited to toluene, diethyl ether, acetone, and acetonitrile.

Solvent/Antisolvent Ratio

In the case of a binary solvent mixture, the formation of the crystalline form can be sensitive to the ratio of solvent to precipitating solvent. For example, if the material is dissolved in ethanol and acetonitrile is added as a precipitating solvent, the ethanol to acetonitrile ratio can vary from 1:1 to 1:4. In this case, the main effect is percent recovery of the crystalline form relative to the starting material. With higher proportions of acetonitrile, a biphasic liquid will form, followed by crystallization of the denser phase.

If slow evaporation is used to obtain crystalline material, a mixture of solvents is required and the ratio of solvents can vary from 4:1 to 1:1.

Solvent/Compound Ratio

The ratio or concentration of compound relative to solvent can be variable depending on the solvent or solvent mixture used. Typical concentrations can range from 150 mg/mL to 10 mg/mL with the limiting factor at the higher end being the solubility of the material or the ease of recovery the material once crystallization has occurred. For example, approximately 150 mg of amorphous material can be dissolved in 1 mL of ethanol with subsequent addition of acetonitrile added to afford the crystalline form.

Temperature Control

In general, the maximum heating temperature used in the above methods can range from 20° C. to the reflux temperature of the solvent. Most typical temperatures range from 20° C. to 60° C. Once a solution has been obtained, and, if required, a precipitating solvent added, the mixture is cooled to room temperature. The rate of cooling can affect the size, shape, and quality of the crystals. If the solution is subjected to prolonged heating over 60° C. or contains a reactive solvent, decomposition can occur.

Rate of Crystallization

Several factors significantly impact the rate of crystallization. These include, but are not limited to: rate of precipitating solvent addition, rate of mixture cooling, and presence of nucleation sites such as dust, seed crystals, or defects on the glass surface. Variations in these parameters can affect the size, shape, and quality of the crystals.

Isolation of the Crystal Form

Several methods for isolation of the desired crystalline form from the supernatant can be used including filtration, decantation, and solvent evaporation. In general, the crystalline form was obtained by collecting any formed solids by vacuum filtration, followed by air-drying and subsequent exposure to high vacuum to remove any residual solvent.

Crystallization by Environmental Modification

In special cases, the desired crystalline form can be obtained by heating a metastable form under vacuum at 60° C. for an extended period. In another case, amorphous material exposed to 75% relative humidity at 40° C. for 2 weeks shows an increase in crystallinity as measured by XRPD.

Procedure for Single X-Ray Data

The single crystal X-ray diffraction studies were carried out on a Bruker Kappa APEX-II CCD diffractometer equipped with Cu $K_a$ radiation ($\lambda$=1.5478). Crystals of the subject compound were grown by adding a several drops of ethanol to the sample vial, which was then heated until all the solid redissolved. The sample was allowed to slowly cool in a sand bath and allowed to sit undisturbed for several days. A 0.417×0.035×0.032 mm piece of a colorless needle was mounted on a Cryoloop with Paratone oil. Data were collected in a nitrogen gas stream at 100(2) K using $\phi$ and $\omega$ scans. Crystal-to-detector distance was 40 mm using variable exposure time (5s-30s) depending on $\theta$ with a scan width of 1.0°. Data collection was 99.7% complete to 60.133° in $\theta$, (0.89 Å) A total of 16248 reflections were collected covering the indices, $-18<=h<=18$, $-5<=k<=5$, $-22<=l<=22$. 4783 reflections were found to be symmetry independent, with a $R_{int}$ of 0.0582. Indexing and unit cell refinement indicated a primitive, monoclinic lattice. The space group was found to be $P2_1$. The data were integrated using the Bruker SAINT software program and scaled using the SADABS software program. Solution by direct methods (SHELXT) produced a complete phasing model consistent with the proposed structure.

All nonhydrogen atoms were refined anisotropically by full-matrix least-squares (SHELXL-2014). All hydrogen atoms were placed using a riding model. Their positions were constrained relative to their parent atom using the appropriate HFIX command in SHELXL-2014. Due to unmodelable solvent disorder, Platon SQUEEZE was used to remove the electron density from the lattice due to the disordered solvent contribution. Solvent appeared to be acetonitrile. One void was found with approximately 34 electrons. The absolute stereochemistry of the molecule was established by anomalous dispersion using the Parson's method with a Flack parameter of 0.033(11). Crystallographic data are summarized in FIG. 4.

Example 1

Synthesis and Direct Conversion of [({[(2R,3S,4R,5R)-5-(6-chloro-4-{[(1S)-1-(2-fluorophenyl)ethyl]amino}-1H-pyrazolo[3,4-b]pyridin-1-yl)-3,4-dihydroxyoxolan-2-yl]methoxy}(hydroxy)phosphoryl)methyl]phosphonic Acid to the Crystalline Form

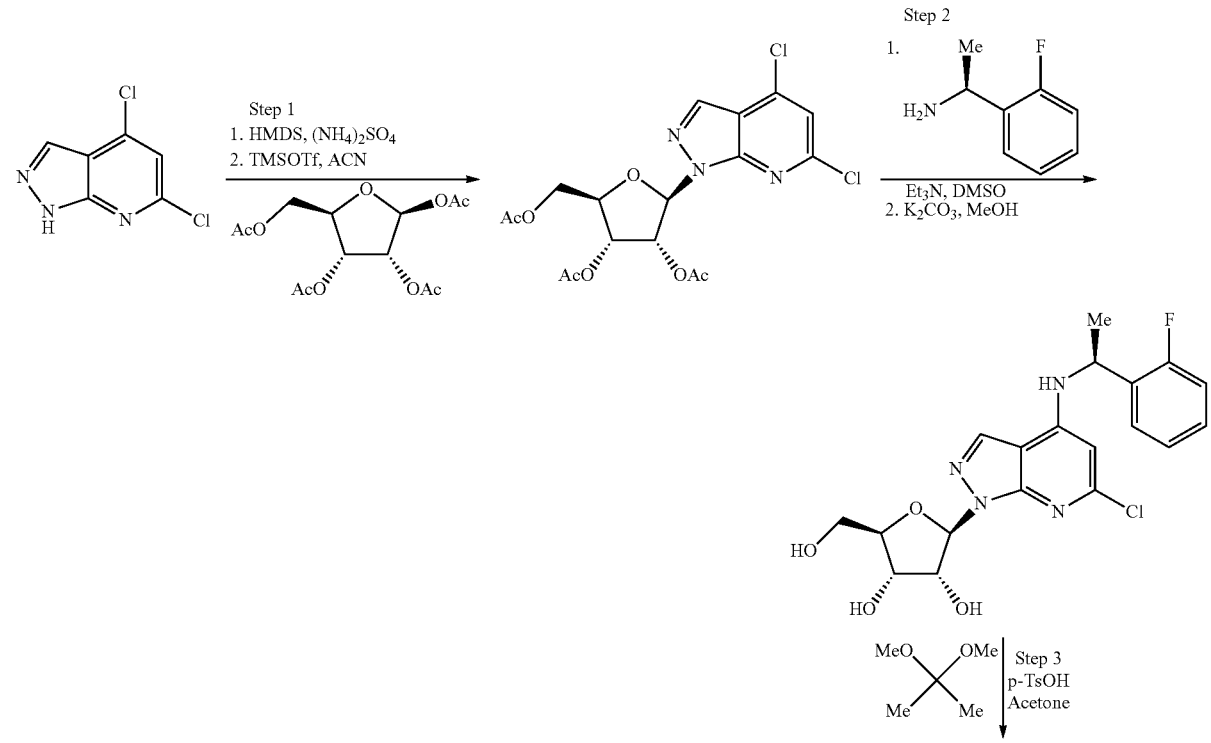

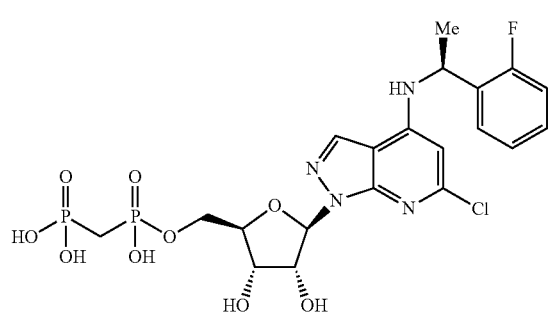

Step 4
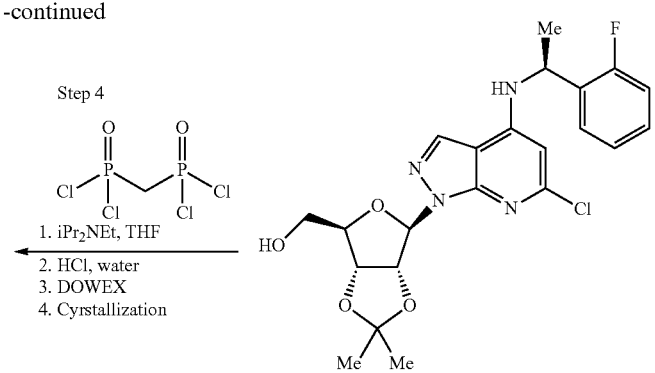
1. iPr₂NEt, THF
2. HCl, water
3. DOWEX
4. Cyrstallization

Step 1: The heterocycle (25 g, 133 mmol) and ammonium sulfate (175 mg, 1 mol %) were charged in a 1 L round bottom flask equipped with a magnetic stir bar. HMDS (133 mL, 1M) was added and the mixture was refluxed for 4 hours under an air atmosphere (heating block temperature 155° C.). Excess HMDS was evaporated under vacuum at 60° C. and then the flask was placed under high vacuum at 45° C. for 30 minutes. This operation was repeated to make sure all excess HMDS was removed.

The pale orange oil residue was dissolved in anhydrous MeCN (266 mL) and the sugar (46.55 g, 146.3 mmol) was added. The resulting mixture was stirred until all the sugar was dissolved (typically 5 min., yellow solution). TMSOTf (4.8 mL, 26.6 mmol) was then added dropwise over 20 minutes (slight exotherm). Upon completion of the TMSOTf addition, LCMS analysis showed that all the starting heterocycle was consumed. The reaction was then stirred for 17-20 hours (deeper colored mixture). An LCMS aliquot showed greater than 90% UV purity with a ratio between the desired product and its glycosidic epimer of 97:3. EtOAc (350 mL) and NaHCO₃$_{(sat.)}$ (300 mL) were successively added at which point the mixture turned deep blue. The layers were separated and the aqueous layer was extracted once with EtOAc (150 mL). The combined organic layers were dried over Na₂S₂O₃, filtered and evaporated to dryness. The deep blue oil was dissolved in DCM (300 mL). Silica (50 g) and activated charcoal (15 g) were added and the resulting suspension was stirred vigorously for 1.5 hours. It was then filtered over Celite to deliver a clear yellow pale to colorless solution. The filtrated was evaporated to dryness to deliver the crude material. The clear oil was dissolved in EtOAc (1.33 mL/g). The solution was stirred vigorously and hexanes (4.5 mL/g) was added at which point a cloudy mixture is obtained. The mixture was heated to reflux until complete dissolution, cooled to room temperature and seeded with seed crystals. After 1 hour at room temperature the mixture was placed in a fridge (0° C.) for 20 hours. The crystals were then filtered and rinsed with cold MTBE (2×80 mL+1×50 mL) to yield pure product (46.85 g, 79%). The mother liquors were evaporated to dryness and the crystallization procedure was repeated. It delivered additional material (4.45 g, 7%). Global yield is 51.3 g, 86%.

Step 2: A 3-neck 5 L round-bottomed flask fitted was charged with a solution of the product from step 1 (157 g, 353 mmol) in dimethyl sulfoxide (353 mL, 1 M). To the solution was added (1S)-1-(2-fluorophenyl)ethylamine.HCl (93 g, 529 mmol, 1.5 equiv) followed by triethylamine (170 mL, 1.2 mol, 3.5 equiv). The reaction mixture was heated to 80° C. and stirred with an overhead mechanical stirrer for 48 h. The mixture was cooled to room temperature and diluted with methanol (700 mL, 0.5 M). K₂CO₃ (233 g, 1.2 mol, 3.5 equiv) was added and the reaction stirred at room temperature. After 40 h, the reaction mixture was filtered through celite and the filter cake was washed with methanol (2×200 mL). The solution was concentrated in vacuo to remove volatiles. To the remaining solution was added 3.5 L of water while stirring vigorously. The resulting precipitate was then collected and washed with water (3×1 L) to afford the desired product as a tan solid (139 g, 92%).

Step 3: To a solution of the product from step 2 (45.74 g, 108 mmol) and 2,2-dimethoxypropane (66.3 ml, 541 mmol) in acetone (270 mL) at room temperature was added p-TsOH (2.05 g, 10.8 mmol). The reaction was stirred for two hours then concentrated under reduced pressure. The crude amber oil was reconstituted in EtOAc (1.0 L) and washed with saturated NaHCO₃ (500 mL). The organic layer was separated and stirred with activated charcoal then filtered. The filtrate was dried over Na₂SO₄, filtered and concentrated in vacuo to provide an off-white solid. The solid was suspended with 1:1 EtOAc:hexanes (500 mL) and collected via vacuum filtration. The filter cake was washed with hexane (100 mL) then dried under high vacuum to afford the desired product as a white solid (39.2 g, 78%).

Step 4: To a suspension of methylenebis(phosphonic dichloride) (81.0 g, 324 mmol, 3.0 equiv) in THF (162 mL, 2.0 M) at 0° C. was added N,N-diisopropylethylamine (20.7 mL, 119 mmol, 1.1 equiv). To the resulting mixture was added a solution of the product from step 3 (50.0 g, 108 mmol, 1.0 equiv) in THF (347 mL, 0.31 M) dropwise over the course of 1 h. Following addition, the resulting mixture was stirred at 0° C. for an additional 15 minutes, then the solution was transferred via cannula to a pre-cooled (0° C.) flask containing 0.2 M HCl (1080 mL). The reaction mixture was warmed to 30° C. and stirred at 30° C. for 16 h [acetonide deprotection]. Upon completion, the reaction mixture was washed with 1.5:1 MTBE/THF (5×900 mL). The aqueous phase was diluted with brine (960 mL) and extracted with 2:1 2-MeTHF/THF (1 L). The organic phase was collected and then washed with brine (2×500 mL). To the organic layer was added DOWEX Marathon C H⁺ Form (20 g/L, 20 g) and stirred for 2 hours at room temperature. The DOWEX beads were removed by filtration and the resulting solution was concentrated under reduced pressure to afford a colorless/off-white foam.

To form the desired crystalline form, the solid was dissolved in EtOH (313 mL) with stirring and then CH₃CN (1,175 mL) was added over the course of 5 minutes. The resulting clear solution was stirred at 25° C. for 1 h, during which time crystallization occurred. The mixture was allowed to sit at 25° C. for 12 h, and then the white solid was collected by vacuum filtration, rinsed with 6:1 CH₃CN/EtOH (150 mL), and dried under reduced pressure for 4 days to afford the product as a white solid (32.6 g, 52% yield, 98.5% UV purity, containing 0.75 wt. % CH₃CN). The solid was subsequently dried in a vacuum oven at 60° C. for 16 h to remove residual CH₃CN and convert the solid to the most thermodynamically stable polymorph.

The crystalline form of the desired material can be generated across a variety of scales, from 1 g to 1 kg, demonstrating this method is reproducible and robust.

Example 2

Stability and Hygroscopicity of Crystalline [({[(2R,3S,4R,5R)-5-(6-chloro-4-{[(1S)-1-(2-fluorophenyl)ethyl]amino}-1H-pyrazolo[3,4-b]pyridin-1-yl)-3,4-dihydroxyoxolan-2-yl]methoxy}(hydroxy)phosphoryl)methyl]phosphonic Acid Vials containing a quantity of the crystalline material were subjected to a temperature of 40° C. at 75% relative humidity (RH) for one week. Analysis by HPLC and XRPD indicated the material showed a decrease in purity from 99% to 97.3% and conversion to the amorphous material. In contrast, a quantity of the crystalline material was subjected to a temperature of 25° C. at 60% relative humidity (RH) for one week and showed no change in crystallinity.

Vials containing a quantity of the crystalline material were subjected to a temperature of 80° C. for one week. Analysis by HPLC and XRPD showed indicated the material showed a decrease in purity from 99% to 97.4% but no change in morphology was observed.

A quantity of the crystalline material was analyzed by dynamic vapor sorption (DVS). The sample was subjected to a ramping profile from 40-90% RH at 10% increments, maintaining the sample at each step until a stable weight had been achieved at 25° C. After completion of the sorption cycle, the sample was dried using the same procedure to 0% RH followed by a second sorption cycle back to 40% RH. Two cycles were performed overall. The weight change during the sorption/desorption cycles were plotted, allowing for the hygroscopic nature of the sample to be determined. Significant hysteresis was observed, with the material retaining much larger quantities of water during the second sorption cycle as shown in FIG. 10. This change in water capacity is associated a phase change, as XRPD of the sample post-DVS shows loss of crystallinity and regeneration of amorphous material. At 90% relative humidity, the material shows an increase of 13.2% wt. water relative to 0% relative humidity, indicating the material is hygroscopic. The amount of water in the sample at 90% relative humidity corresponds to the pentahydrate of the material.

Example 3

Summary of Solid forms: Form A, Form B, Form C and Form D

Using methods of single solvent heating, binary solvent mixture heating, and slow evaporation, a variety of conditions were identified which yielded crystalline forms of the material. Crystallinity was initially determined through the melting range of the material, in which crystalline compounds exhibit relatively sharp and higher melting ranges compared the amorphous material. In one instance, amorphous material obtained through lyophilization exhibited a melting range of 132-164° C.; in contrast, crystalline material obtained through addition of acetonitrile to a room temperature solution of compound and ethanol exhibited a melting range of 161-166° C. Summaries of selected conditions are shown in FIG. 5.

As evident from FIG. 5, melting point measurements on the material obtained from different solvent combinations suggest two significantly crystalline forms of the material can be obtained. The highest melting form (Form A) observed melted at approximately 164-170° C. and was obtained by heating a metastable form (Form B) under vacuum at 60° C. for an extended period. This second form (Form B) melted at approximately 161-166° C. and was generally obtained by crystallization using an alcoholic solvent and acetonitrile as a precipitating solvent. Comparison of XPRD analyses of Forms A and B in FIG. 1 and FIG. 6 confirms the differences in crystalline form between the two samples.

FIG. 7 shows the DSC trace of Form B, with a major endotherm occurring at a lower temperature compared to the DSC trace of Form A in FIG. 2, consistent with the form having a lower observed melting point. Following the major endotherm in FIG. 7, a smaller endotherm corresponding to the melting temperature of Form A is observed, suggesting small amounts of Form A are produced during data collection or are already present in the native material.

NMR analysis of Form B shows that significant amounts of acetonitrile are present, suggesting Form B may exist as a solvate. In contrast, Form A contains only trace amounts of acetonitrile.

In addition to Forms A and B, Form C (FIG. 8) and Form D (FIG. 9) of the material were also synthesized. These forms are significantly less crystalline compared to Forms A and B. DTA analysis of Form D did not exhibit any prominent thermal events.

Form A (melting point 164-170° C.) can be assigned as the most stable form based on DSC data indicating the phase transition occurs at 168° C. compared to the transition of Form B which occurs at 145° C. Additional support is provided by the fact that Form B irreversibly converts to Form A upon heating.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A solid form of a compound of Formula (I):

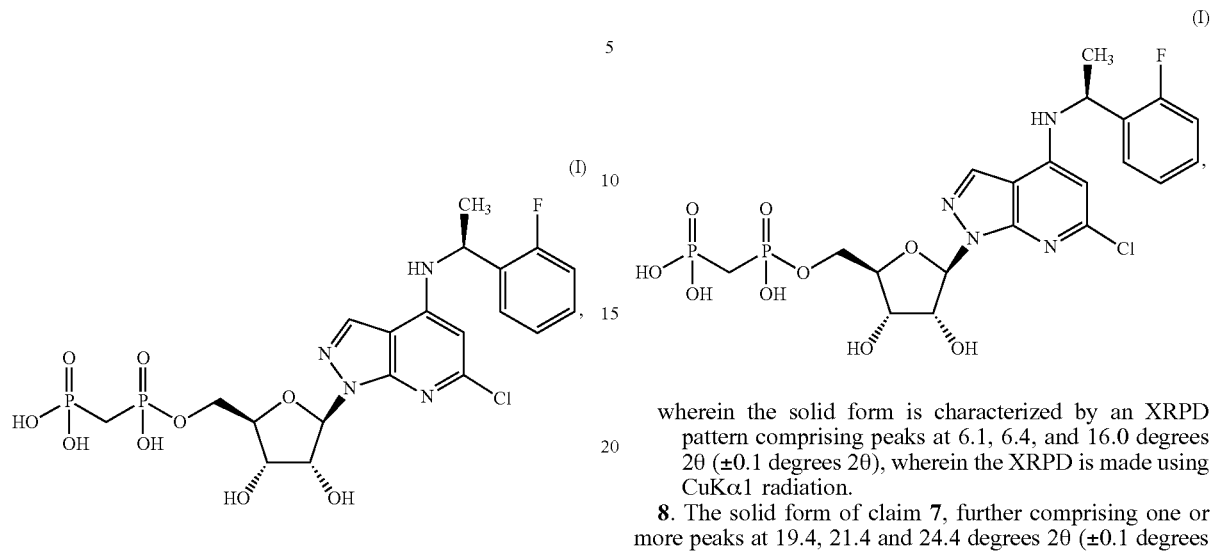

wherein the solid form is characterized by an XRPD pattern comprising peaks at 5.5, 6.6, and 22.7 degrees 2θ (±0.1 degrees 2θ), wherein the XRPD is made using CuKα1 radiation.

2. The solid form of claim 1, further comprising one or more peaks at 10.4, 11.0, 19.7, or 21.2 degrees 2θ (±0.1 degrees 2θ), wherein the XRPD is made using CuKα1 radiation.

3. The solid form of claim 1, characterized by an XRPD pattern having peaks at 5.5, 6.6, 10.4, 12.9, 15.2, 16.5, 17.2, 17.7, 19.7, 20.3, 21.2, 22.7, 24.0, 25.3, 25.6, 28.2, and 30.3 degrees 2θ (±0.1 degrees 2θ), wherein the XRPD is made using CuKα1 radiation.

4. The solid form of claim 1, characterized by an XRPD pattern substantially in accordance with that of FIG. 6.

5. The solid form of claim 1, characterized by a differential scanning calorimetry (DSC) pattern having an endotherm at about 145° C.

6. The solid form of claim 1, characterized by a differential scanning calorimetry (DSC) pattern substantially in accordance with that of FIG. 7.

7. A solid form of a compound of Formula (I):

wherein the solid form is characterized by an XRPD pattern comprising peaks at 6.1, 6.4, and 16.0 degrees 2θ (±0.1 degrees 2θ), wherein the XRPD is made using CuKα1 radiation.

8. The solid form of claim 7, further comprising one or more peaks at 19.4, 21.4 and 24.4 degrees 2θ (±0.1 degrees 2θ), wherein the XRPD is made using CuKα1 radiation.

9. The solid form of claim 7, characterized by an X-ray powder diffraction pattern (XRPD) having peaks at 6.1, 6.4, 10.1, 11.7, 16.0, 16.6, 18.1, 19.4, 21, 21.4, 21.9, 22.4, 24.4, 25.6, 27.3, 28.3, and 29.4 degrees 2θ (±0.1 degrees 2θ), wherein the XRPD is made using CuKα1 radiation.

10. The solid form of claim 7, characterized by an X-ray powder diffraction pattern (XRPD) substantially in accordance with that of FIG. 1.

11. The solid form of claim 7, characterized by a unit cell as determined by single crystal X-ray diffraction of the following dimensions: a=16.6099(8) Å; b=4.8116(2) Å; c=20.0513(11) Å; α=90°; β=90.386(2°); and γ=90°.

12. The solid form of claim 7, characterized by a differential scanning calorimetry (DSC) pattern having an endotherm at about 168° C.

13. The solid form of claim 7, characterized by a differential scanning calorimetry (DSC) pattern substantially in accordance with that of FIG. 2.

14. A pharmaceutical composition comprising a solid form of claim 1, and a pharmaceutically acceptable excipient.

15. A pharmaceutical composition comprising a solid form of claim 7, and a pharmaceutically acceptable excipient.

16. A method of treating a disease, disorder, or condition, mediated at least in part by CD73, said method comprising administering an effective amount of a solid form of claim 1 to a subject in need thereof.

17. A method of treating a disease, disorder, or condition, mediated at least in part by CD73, said method comprising administering an effective amount of a solid form of claim 7 to a subject in need thereof.

* * * * *

UNITED STATES PATENT AND TRADEMARK OFFICE
CERTIFICATE OF CORRECTION

| | |
|---|---|
| PATENT NO. | : 11,819,512 B2 |
| APPLICATION NO. | : 17/311945 |
| DATED | : November 21, 2023 |
| INVENTOR(S) | : Jeffrey et al. |

It is certified that error appears in the above-identified patent and that said Letters Patent is hereby corrected as shown below:

In the Claims

In Claim 8, Column 40, Line 24, please replace "wherein the XRPD is made using $CuK_{\alpha 1}$ radiation." with --wherein the XRPD is made using CuKα1 radiation.--.

In Claim 9, Column 40, Line 27, please replace "10.1, 11.7, 16.0, 16.6, 18.1, 19.4, 21, 21.4, 21.9, 22.4, 24.4," with --10.1, 11.7, 16.0, 16.6, 18.1, 19.4, 21.0, 21.4, 21.9, 22.4, 24.4,--.

In Claim 9, Column 40, Line 29, please replace "wherein the XRPD is made using $CuK_{\alpha 1}$ radiation." with --wherein the XRPD is made using CuKα1 radiation.--.

Signed and Sealed this
Twenty-third Day of July, 2024

*Katherine Kelly Vidal*

Katherine Kelly Vidal
*Director of the United States Patent and Trademark Office*